(12) United States Patent
Izhikevich et al.

(10) Patent No.: US 8,712,941 B2
(45) Date of Patent: Apr. 29, 2014

(54) ELEMENTARY NETWORK DESCRIPTION FOR EFFICIENT LINK BETWEEN NEURONAL MODELS AND NEUROMORPHIC SYSTEMS

(75) Inventors: Eugene M. Izhikevich, San Diego, CA (US); Csaba Petre, San Diego, CA (US); Filip Piekniewski, San Diego, CA (US); Botond Szatmary, San Diego, CA (US)

(73) Assignee: Brain Corporation, San Diego, CA (US)

( * ) Notice: Subject to any disclaimer, the term of this patent is extended or adjusted under 35 U.S.C. 154(b) by 256 days.

(21) Appl. No.: 13/239,148

(22) Filed: Sep. 21, 2011

(65) Prior Publication Data

US 2013/0073498 A1    Mar. 21, 2013

(51) Int. Cl.
| | |
|---|---|
| G06F 15/18 | (2006.01) |
| G06N 3/10 | (2006.01) |
| G06F 19/12 | (2011.01) |
| G06F 9/50 | (2006.01) |
| G06F 19/00 | (2011.01) |

(52) U.S. Cl.
CPC .......... *G06F 9/5011* (2013.01); *G06F 19/3437* (2013.01)
USPC .................... 706/27; 706/25; 706/26; 706/44

(58) Field of Classification Search
USPC .......................................................... 706/27
See application file for complete search history.

(56) References Cited

U.S. PATENT DOCUMENTS

| 6,009,418 A | 12/1999 | Cooper |
| 2005/0015351 A1 | 1/2005 | Nugent |
| 2007/0176643 A1 | 8/2007 | Nugent |
| 2009/0043722 A1 | 2/2009 | Nugent |
| 2011/0016071 A1 | 1/2011 | Guillen et al. |
| 2011/0119214 A1 | 5/2011 | Breitwisch et al. |
| 2012/0011090 A1 | 1/2012 | Tang et al. |
| 2012/0109866 A1 | 5/2012 | Modha |

FOREIGN PATENT DOCUMENTS

WO    2008083335    7/2008

OTHER PUBLICATIONS

Gewaltig et al. (Gewaltig), "NEST (NEural Simulation Tool)", 2007.*
Fidjeland et al., Accelerated Simulation of Spiking Neural Networks Using GPUs [online], 2010 [retrieved on Jun. 15, 2013]. Retrieved from the Internet:<URL: http://ieeexplore.ieee.org/xpls/abs_all.jsp?arnumber=5596678&tag=1>.*
Brette et al., Brian: a simple and flexible simulator for spiking neural networks, The Neuromorphic Engineer, Jul. 1, 2009, pp. 1-4, doi: 10.2417/1200906.1659.

(Continued)

*Primary Examiner* — Jeffrey A Gaffin
*Assistant Examiner* — Nathan Brown, Jr.
(74) *Attorney, Agent, or Firm* — Pillsbury Winthrop Shaw Pittman LLP

(57) ABSTRACT

A simple format is disclosed and referred to as Elementary Network Description (END). The format can fully describe a large-scale neuronal model and embodiments of software or hardware engines to simulate such a model efficiently. The architecture of such neuromorphic engines is optimal for high-performance parallel processing of spiking networks with spike-timing dependent plasticity. The format is specifically tuned for neural systems and specialized neuromorphic hardware, thereby serving as a bridge between developers of brain models and neuromorphic hardware manufactures.

21 Claims, 14 Drawing Sheets

(56) References Cited

OTHER PUBLICATIONS

Goodman et al., Brian: a simulator for spiking neural networks in Python, Frontiers in Neuroinformatics, Nov. 2008, pp. 1-10, vol. 2, Article 5.

Djurfeldt, Mikael, The Connection-set Algebra: a formalism for the representation of connectivity structure in neuronal network models, implementations in Python and C++, and their use in simulators, BMC Neuroscience, Jul. 18, 2011, p. 1, 12(Suppl 1):p. 80.

Gewaltig et al., NEST (NEural Simulation Tool), Scholarpedia, 2007, pp. 1-15, 2(4):1430, doi:10.4249/scholarpedia.1430.

Gleeson et al., ) NeuroML: A Language for Describing Data Driven Models of Neurons and Networks with a High Degree of Biological Detail, PLoS Computational Biology, Jun. 2010, pp. 1-19. vol. 6, Issue 6.

Gorchetchnikov et al., NineML: declarative, mathematically-explicit descriptions of spiking neuronal networks, Frontiers in Neuroinformatics, Conference Abstract: 4th INCF Congress of Neuroinformatics, doi: 10.3389/conf.fninf.2011.08.00098.

Davison et al., PyNN: a common interface for neuronal network simulators, Frontiers in Neuroinformatics, Jan. 2009, pp. 1-10, vol. 2, Article 11.

Graham, Lyle J., The Surf-Hippo Reference Manual, http://www.neurophys.biomedicale.univ-paris5.fr/~graham/surf-hippo-files/Surf-Hippo%20Reference%20Manual.pdf, Mar. 2002, pp. 1-128.

Bohte, "Spiking Nueral Networks" Doctorate at the University of Leiden, Holland, Mar. 5, 2003, pp. 1-133 [retrieved on Nov. 14, 2012]. Retrieved from the internet: <URL: http://homepages.cwi.nl/-sbohte/publication/phdthesis.pdf>.

Izhikevich, "Polychronization: Computation with Spikes", Neural Computation, 25, 2006, 18, 245-282.

Izhikevich, "Simple Model of Spiking Neurons", IEEE Transactions on Neural Networks, vol. 14, No. 6, Nov. 2003, pp. 1569-1572.

Karbowski et al., "Multispikes and Synchronization in a Large Neural Network with Temporal Delays", Neural Computation 12, 1573-1606 (2000).

PCT International Search Report and Written Opinion for Int'l application No. PCT/US2012/055933, dated Dec. 4, 2012.

Laurent, "The Neural Network Query Language (NNQL) Reference" [retrieved on Nov. 12, 2013]. Retrieved from the Internet: <URL:http://nnql.org/nnql.org>.

Laurent, "Issue 1—nnql—Refactor Nucleus into its own file—Neural Network Query Language" [retrieved on Nov. 12, 2013]. Retrieved from the Internet: <URL:https://code.google.com/p/nnql/issues/detail?id=1>.

\* cited by examiner

US 8,712,941 B2

ELEMENTARY NETWORK DESCRIPTION FOR EFFICIENT LINK BETWEEN NEURONAL MODELS AND NEUROMORPHIC SYSTEMS

This application is related to U.S. patent application Ser. No. 13/239,123, filed contemporaneously herewith and entitled "Elementary Network Description For Neuromorphic Systems," U.S. patent application Ser. No. 13/239,155, filed contemporaneously herewith and entitled "Elementary Network Description For Efficient Memory Management In Neuromorphic Systems," U.S. patent application Ser. No. 13/239,163, filed contemporaneously herewith and entitled "Elementary Network Description For Efficient Implementation Of Event-Triggered Plasticity Rules In Neuromorphic Systems," U.S. patent application Ser. No. 13/239,255, filed contemporaneously herewith and entitled "Apparatus And Methods For Synaptic Update In A Pulse-Coded Network," and to U.S. patent application Ser. No. 13/239,259, filed contemporaneously herewith and entitled "Apparatus And Method For Partial Evaluation Of Synaptic Updates Based On System Events," each of the foregoing applications being commonly owned and incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates generally to parallel distributed computer systems for simulating neuronal networks that perform neural computations, such as visual perception and motor control.

2. Description of Related Art

Most neuronal models and systems consist of networks of simple units, called neurons, which interact with each other and with the external world via connections called synapses. The information processing in such neuronal systems is carried out in parallel.

There are many specialized software tools that help neuroscientists to simulate models of neural systems. These tools include NEURON, GENESIS, NEST, BRIAN, and many other freely available software tools that simulate biologically plausible and anatomically realistic models. These tools are designed with the view to make the design of such models convenient for neuroscientists. However, the tools are cumbersome to be used to design optimized software or hardware engines to simulate such models efficiently, especially when real-time performance is required, as in autonomous robotics applications.

In contrast, there are many low-level languages, such as assembly languages, LLVM (low-level virtual machine) language, Java Bytecode, chip instruction sets, etc., that are designed for efficient hardware implementations on x86, ARM, and other silicon chips. However, such languages are ill appropriate for parallel simulations of neuronal systems, mostly because the silicon chips are not designed for such parallel neuronal simulations.

There is obviously a need to have parallel hardware architectures and corresponding languages that are optimized for parallel execution and simulation of neuronal models.

SUMMARY OF THE INVENTION

The present invention satisfies the foregoing needs by providing, inter alia, apparatus and methods for elementary network description for neuromorphic systems.

Certain embodiments of the invention provide neuronal networks and methods for configuring a neuronal network. A specification of a system may be parsed where the system exhibits aspects of a neuronal network that includes a plurality of independently executable threads. Each of the threads is mapped onto a neuronal network comprising a plurality of doublets where each doublet may be connected to a presynaptic unit and a postsynaptic unit. Each doublet can be configured to modify a memory of the postsynaptic unit responsive to events received from the presynaptic unit. Operational characteristics of the plurality of doublets can be defined together with their corresponding presynaptic and postsynaptic units. Defining the operational characteristics may include configuring a doublet event rule for each doublet that determines how the each doublet updates the memory of the postsynaptic unit, wherein execution of doublet event rules is order-independent. Defining the operational characteristics may include configuring a unit update rule for each unit that controls the response of the each unit to memory updates initiated by a doublet. Execution of the unit update rules can be order-independent.

In certain embodiments, configuring doublet event rules includes configuring each of the doublet event rules to be executed within a time step during which an event is received, where the time step has a duration determined by a system clock. Each presynaptic unit may maintain an event condition that controls transmission of events to a connected doublet. One or more doublets can have a doublet memory. Doublet event rules can be configured to determine how doublets update their doublet memory. The doublet event rule for each doublet may include a timing event rule that controls modification of a memory of the each doublet based on timing of pulses associated with one or more of the plurality of units. Execution of the doublet event rule for each doublet may be triggered by an event received from a presynaptic unit.

In certain embodiments, the neuronal network comprises a plurality of triplets, each triplet adapted to access memory of a pair of units. Each triplet can have a memory and may be configured to modify its own memory and the memory of at least one of the pair of units. Mapping each of the threads onto a neuronal network may comprises configuring triplet update rules that control updates to memories of triplets and their corresponding pairs of triplet-connected units, wherein execution of triplet update rules is order-independent. Each step of configuring rules can be performed in accordance with a directed graph representative of the neuronal network. The step of mapping may include producing an abstracted hardware mapping representing the neuronal network. The hardware mapping can be described in a hardware description language.

Certain embodiments comprise configuring a semiconductor integrated circuit to implement the neuronal network. Each of the threads may be mapped onto a neuronal network using one or more target libraries that describe units and doublets as constructs in an abstracted description language that is independent of target characteristics. Mapping each of the threads onto a neuronal network can comprise mapping each thread onto abstracted units and doublets to obtain an abstracted description of the neuronal network. A definition of a physical implementation of the neuronal network may be generated using a synthesis tool from the abstracted description of the neuronal network. Configuring the rules can comprise providing one or more rule libraries that describe the rules in an abstracted programming language. Configuring the rules may comprise generating abstracted rules using the one or more rule libraries and coded in the abstracted programming language. The physical implementation of the neuronal network may be configured by compiling the abstracted rules into object code consistent with the physical implementation of the neuronal network.

Further features of the present invention, its nature and various advantages will be more apparent from the accompanying drawings and the following detailed description.

Figure 1:
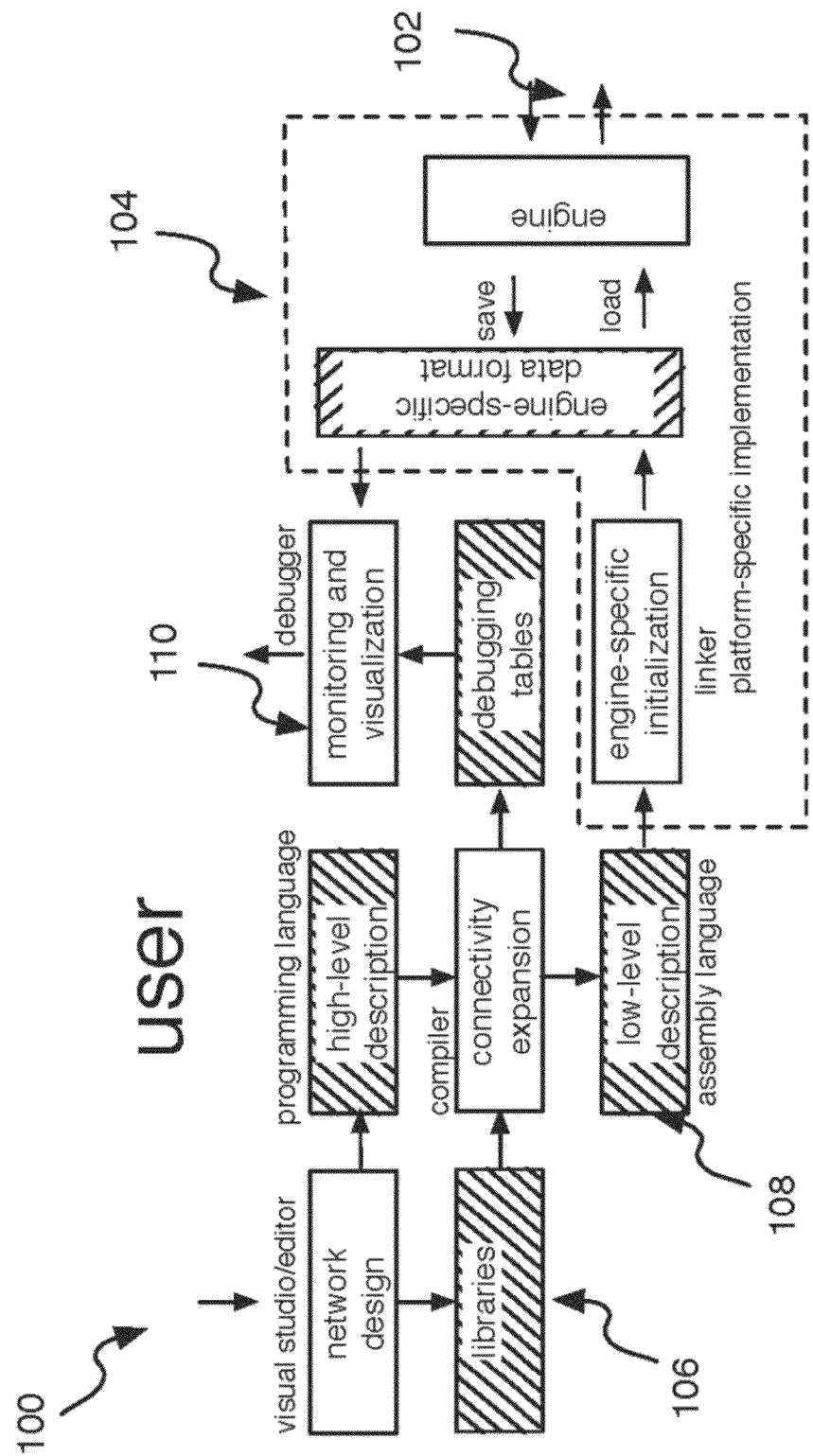
FIG. 1 is a block diagram depicting neural simulator according to one embodiment of the invention

All Figures disclosed herein are ©Copyright 2011 Brain Corporation. All rights reserved.

DETAILED DESCRIPTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of or combination with some or all of the described or illustrated elements. Wherever convenient, the same reference numbers will be used throughout the drawings to refer to same or like parts.

Where certain elements of these embodiments can be partially or fully implemented using known components, only those portions of such known components that are necessary for an understanding of the present invention will be described, and detailed descriptions of other portions of such known components will be omitted so as not to obscure the invention.

In the present specification, an embodiment showing a singular component should not be considered limiting; rather, the invention is intended to encompass other embodiments including a plurality of the same component, and vice-versa, unless explicitly stated otherwise herein.

Further, the present invention encompasses present and future known equivalents to the components referred to herein by way of illustration.

As used herein, the terms "computer", "computing device", and "computerized device", include, but are not limited to, personal computers (PCs) and minicomputers, whether desktop, laptop, or otherwise, mainframe computers, workstations, servers, personal digital assistants (PDAs), handheld computers, embedded computers, programmable logic device, personal communicators, tablet computers, portable navigation aids, J2ME equipped devices, cellular telephones, smart phones, personal integrated communication or entertainment devices, or literally any other device capable of executing a set of instructions and processing an incoming data signal.

As used herein, the term "computer program" or "software" is meant to include any sequence or human or machine cognizable steps which perform a function. Such program may be rendered in virtually any programming language or environment including, for example, C/C++, C#, Fortran, COBOL, MATLAB™, PASCAL, Python, assembly language, markup languages (e.g., HTML, SGML, XML, VoXML), and the like, as well as object-oriented environments such as the Common Object Request Broker Architecture (CORBA), Java™ (including J2ME, Java Beans, etc), Binary Runtime Environment (e.g., BREW), and the like.

As used herein, the terms "connection", "link", "transmission channel", "delay line", "wireless" means a causal link between any two or more entities (whether physical or logical/virtual), which enables information exchange between the entities.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), MEMRISTOR memory, and PSRAM.

As used herein, the terms "microprocessor" and "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable computer fabrics (RCFs), array processors, secure microprocessors, and application-specific integrated circuits (ASICs). Such digital processors may be contained on a single unitary IC die, or distributed across multiple components.

As used herein, the terms "event", "action potential", "pulse", "spike", "burst of spikes", and "pulse train" are meant generally to refer to, without limitation, any type of a pulsed signal, e.g., a rapid change in some characteristic of a signal, e.g., amplitude, intensity, phase, or frequency, from a baseline value to a higher or lower value, followed by a rapid return to the baseline value and may refer to any of a single spike, a burst of spikes, an electronic pulse, a pulse in voltage, a pulse in electrical current, a software representation of a pulse and/or burst of pulses, a software representation of a latency or timing of the pulse, and any other pulse or pulse type associated with a pulsed transmission system or mechanism. As used herein, the term "spnet" includes the spiking network described in the Izhikevich publication of 2006 and titled: "Polychronization: Computation with Spikes."

Detailed descriptions of the certain embodiments of the invention, including systems, apparatus and methods, are disclosed herein. Although certain aspects of the invention can best be understood in the context of parallel simulation engine architecture, implemented in software and hardware, which can efficiently simulate large-scale neuronal systems, embodiments of the invention may also be used for implementing an the instruction set—Elementary Network Description (END) format—that is optimized for efficient representation of neuronal systems in hardware-independent manner.

For example, certain embodiments may be deployed in a hardware and/or software implementation of a neuromorphic computer system. In one such implementation, an image processing system may include a processor embodied in an application specific integrated circuit ("ASIC"), which can be adapted or configured for use in an embedded application such as a prosthetic device.

EXAMPLE

Outline of a Development Environment

Referring now to the example depicted in FIG. 1, one configuration of a neural simulator development environment 100 is shown and described in detail. In this example, network design, connectivity expansion, monitoring and visualization, engine-specific initialization, and engine blocks may comprise software tools while labeled libraries, high level description, debugging tables, low level description and engine-specific data format blocks may be implemented as data structures in specific formats which are described in more detail herein.

The neural simulator development environment of FIG. 1 allows a user to define an arbitrary neural system model and to execute the model on an arbitrary computational platform (the engine). Neural simulator development 100 may comprise a number of software tools (transparent blocks in FIG. 1) that interact with each other via data structures configured in certain formats, and a computational engine 104, which can be embodied in a single computer, a computer cluster, GPU, or a specialized hardware. In certain embodiments, the computational engine 104 may be a part of computerized control/sensory input processing apparatus and exchanges data with the rest of the apparatus via a pair of arrows 102 in FIG. 1. By way of example, the computational engine 104 receives sensory information from the "real world" via the input 102 and sends motor commands to any appropriate actuators (not shown) of the control apparatus via the output 103 enabling the control/processing respond to the sensory inputs via a set of drivers.

Typically, a user specifies the desired network layout of the neural simulator 100 using a GUI network design tool, e.g., similar to Microsoft Visual Studio™. In one example, the neural simulator employs specialized libraries, configured to implement various specialized functions. Some specific library modules may be, for example, described briefly as "retina+thalamus+V1 with 1M neurons". In another embodiment, the library modules may be described in more detail, providing initialization of various default parameters (as appropriate) that define, e.g., plasticity, neuronal dynamics, cortical microcircuitry, etc. The GUI network design tool saves the network layout of the neural simulator 100 in a "high-level description" format. In one example, the GUI network design tool is configured to modify the libraries 106 in FIG. 1.

The high-level description of the network layout is compiled into a low-level description (Elementary Network Description—END) 108 using the libraries 106. For example, the high-level description may comprise description of cortical areas V1 and V2 (not shown) and require connecting them according to an appropriate connectivity rule stored in the library 106. The compiler allocates neurons, establishes the connections between the neurons, etc., and saves the network layout 100 in a low-level description that is similar to an assembly language. In one example, the compiler may provide appropriate tables for monitoring and visualization tool during debugging.

Figure 2:
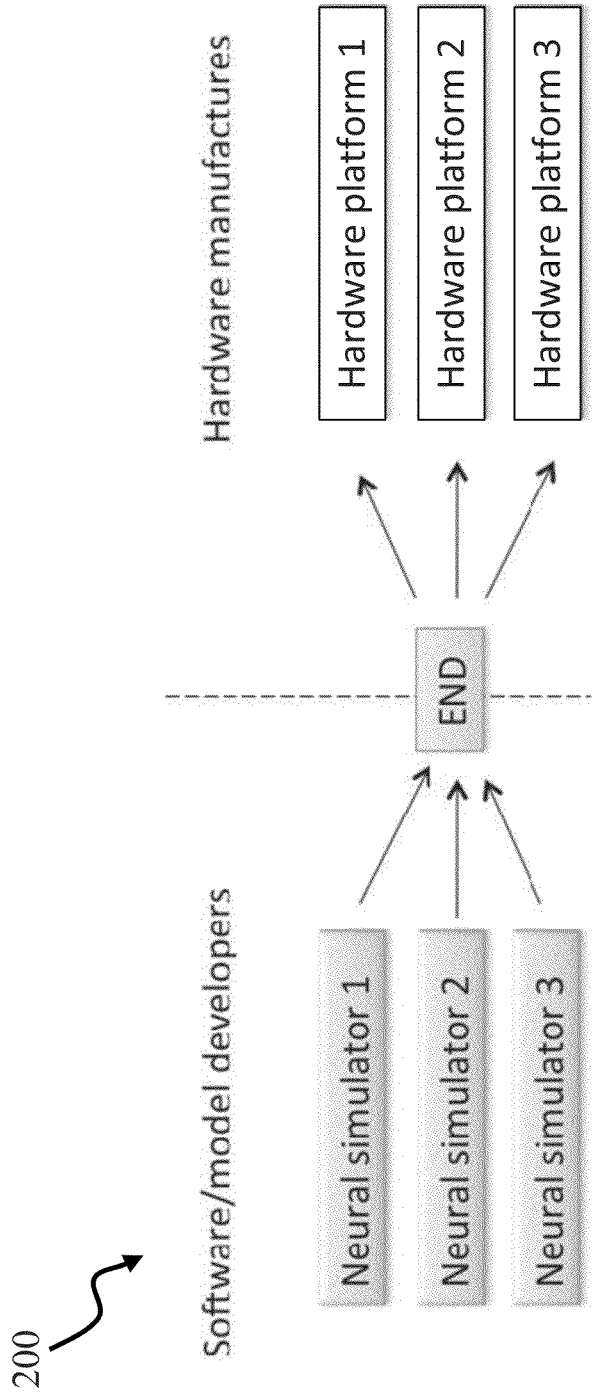
FIG. 2 is a block diagram illustrating one implementation of model development workflow according to the invention.

The Elementary Network Description (END) representation acts as an intermediary bottleneck (i.e., a link) between simulator tools and hardware platform implementations as illustrated in FIG. 2. The END representation provides an abstraction layer that isolates developing environment from the underlying hardware. One objective of END is to isolate the step of developing neural network models from hardware simulation tools, as illustrated in FIG. 2. The END approach may operate to partition implementation of neural models (such as the model of FIG. 1) into two steps. At the first step, neuroscientists create neural models of varying complexity using high-level description language and END representation. At the second step, developers (programmers and hardware engineers) modify and adapt underlying implementation blocks to adapt and optimize model operation for a particular hardware/software platforms, etc. In this architecture, the END format performs the same services as LLVM (low-level virtual machine) or Java bytecode; however, the END format can be optimized for parallel representation and execution of neuronal systems.

The low-level description of the model is converted to the engine-specific binary form suitable for upload to the computational engine 104, as shown in FIG. 1. The computational engine is capable of saving its current state in the same format for subsequent re-uploading. The binary data is used by the monitoring and visualization block 110 of FIG. 1 during debugging and visualization of computation results and monitoring of the system. As described above, the computational engine interacts with the real world via sensors and actuators (connected to the hardware by drivers) as depicted by the arrows 102 in FIG. 1.

Elementary Network Description

The elementary network description (END) of the network comprises the lowest-level platform-independent model depiction. In one implementation, such description is configured similarly to assembly language description, commonly used in computer programming arts. However, while most existing computer assembly language implementations are processor-dependent, the END description is hardware-agnostic.

The END description may also operate as a platform-independent link between a high-level description and the platform-specific implementation of the neural model, as illustrated in FIG. 2. In FIG. 2, blocks 210 (Neural simulators 1-3)

denote various network development tools (such as, NEURON, GENESIS, NEST), while blocks 220 (Hardware platform 1-3) denote different hardware implementations (e.g., CPU, multiprocessor computers (workstations, desktop, server, mainframe, ASICs, FPGA, etc) that are used to execute the respective neural simulator models.

In one embodiment of the END implementation, input neural simulator model data is provided in an XML format (or any other convenient structured data format) or in a relational database normal form aimed at providing minimal set of input data that is sufficient to specify exactly and completely every aspect of neural simulation model, including but not limited to every neuron, dendritic tree, synapse, neuronal and synaptic classes, plasticity rules, neuronal dynamics, etc. This set of input data is configured via multiple relations between the above items. This set of input data may be configured in a variety of ways: (i) a collection of multiple flies each describing a single data structure, e.g., a neuron; (ii) a single file (that may be compressed); or (iii) hierarchical directory/folder/file structure; or a combination thereof.

In one example, the fundamental (atomic) computational unit of the network simulation model is a neuron, referred to as a "unit". In another example the unit comprises a neuronal compartment where the units are linked by junctions to form dendritic trees, which form neurons. In these examples, the synapses comprise connections from one unit to another, thereby enabling to describe unit (node) interconnections via a connectivity graph. Such graphs do not necessarily comprise trees connected to trees through synapses coming from somas.

In order to obtain operational network description, each unit (e.g., neuron, compartment) and each synapse is subject to a set of rules that govern its dynamics. In one example, some of these rules comprise clock-based rules that apply to neuronal units and junctions, while other rules are event-based and apply only to synapses.

By way of example, each neuronal unit may be subject to a set of rules that describe spike-generation mechanism for that unit, comprising: (i) the condition for firing a spike; and (ii) a set of modifications that are applied to the unit dynamic state variables after the spike is fired. Similarly, each synapse is subject to spike rules that determine a set of actions performed on the synapse when a pre-synaptic unit fires and a set of actions performed on the synapse when a post-synaptic unit fires.

In one embodiment, the END format is used to generate a C code that implements the computational engine (e.g., the engine 104 in FIG. 1). In this embodiment, which is referred to herein as END 1.0, the description of rules comprises code strings that are inserted into a C-code template in order to provide the neuronal model with arbitrary expandable functionality, as illustrated by the examples below.

END 1.0 typically implements an object inheritance structure that comprises object classes unit_class, junction_class, synaptic_class, and event_rule with possible subclasses. Each such class has instances, i.e., units, junctions, synapses, and rules.

END 1.0 can be configured to separate the data (units, junctions, synapses) from the methods (update and spike rules), thereby enabling the computational engine (e.g., the linker 112 of the engine 102 in FIG. 1) to implement data ↔ methods interconnections. In some implementations of the computational engine, the computational operations are grouped by data (e.g., for every synapse, all of the actions (rules) are executed for that synapse). In other commonly used implementations of the computational engine, e.g., useful with GPU hardware, computational operations are grouped by methods (e.g., for every update rule, outstanding requests for all synapses that are subject to that update rule are executed). The END can be configured to operate equally well with any of the above operational grouping configurations.

When implementing large-scale models of complex real-life systems such as, for example, a mammalian visual system, certain data structures described by the END format may consume the majority (in one example up to 99%) of the network model resources (memory or CPU, or both). Implementation of these data structures, typically referred to as "canonical structures", greatly benefits from the use of specialized hardware, such as an ASIC or FGPA optimized to simulate such canonical structures. Similarly, in some implementations where certain rules and methods consume majority of CPU processing resources (e.g., take the most time to execute), development of specialized hardware accelerators provides a substantial increased in processing of canonical methods. Different hardware implementations can hard-wire different methods, leading to a diversity of hardware platforms.

One of the goals attained with the END description is to provide the minimal instruction set that is sufficient for describing neuronal models of arbitrary complexity. Herein, the following notation is used in describing the END format: class or type definition type is encased in angle brackets < . . . >; the fields within the class (or type) are indented, with respect to the class definition, as shown in the Definition 1 example, below.

Definition 1

In the above definition, the statement <unit of (unit_class)> denotes definition of an instance of the class "unit_class" having fields "unit_id" and "Initialization" as follows:

---

<unit of (unit_class)>
    unit_id
    Initialization

---

This class defines a neuron or a compartment, but in principle, can be any neural unit, that is executed by the model at a predefined model execution time step (e.g., 1 ms). The unit is an instantiation of the object unit_class that specifies the operations performed at each of the model time steps. The fields of the unit_class are defined as follows:

unit_id is a unique label, e.g., a number or a string, that identifies each unit. Alternatively, the unit_id is a Perl or PHP or RegEx, or MATLAB expression that specifies a range of valid ids, and the actual id is assigned during model build by the linker. For example, 'exc(1:1000)' or 'exc1:exc1000'.

Initialization is a structure containing initial values of the class fields that are different from the default values in the definition of the class. AH these have to be declared and already initialized with default values in the unit_class.

---

<unit_class of (unit_class)>
    unit_class_id
    execution_condition
    update_rule
    event_condition
    after_event_rule
    initialization

--- provides a generic definition of a neuronal model class that specifies neuronal dynamics, allocates neuronal variables, defines spike processing rules, etc. The class <unit_class> is an object (as in object-oriented programming) that can be derived from another object of unit_class. The fields of the <unit_class> object are defined as follows:

unit_class_id is a unique name of the object class (string), E.g., 'exc' or 'p23soma' or 'p4cmprtmnt3'. These object names are used by the neuronal model as names of vectors to refer to the units, e.g., in background processes or in I/O processes.

execution_condition the condition that is evaluated at every model execution time step in order to determine whether or not to execute units of this class, for example: 'now%10==0'; or 'DA>0.1'. If the execution_condition is absent (the field is blank), then respective unit is executed at every model time step (i.e., the system clock step cycle). When a class (subclass) is derived from a base class (superclass), then the derived class execution condition overrides the base class execution condition.

update_rule defines a code string that will be converted by the linker to executable code. In one example, the code string comprises a forward Euler numerical method notation, such as, for example:

| `x(t+1) = x(t) + tau*(F(x(t)) ).` | `'I += g*(E-V); g +=` |
| `tau*(-g)/5;` | |
| `v += tau*( 2*(v+70)*(v+50)−u+I)/20;` | `u += tau*0.1*(2*(v+70)−` |
| `u);`. | |

In another example, the code string specifies mapping x(t+1)='x(t)+tau*(f(x(t))' or a C-executable code (function or subroutine) that are performed at each step of model execution. When the class is derived from a base class, then the object update_rule of the subclass is executed first, followed by the base class rule, thereby allowing for update of certain variable by the subclass rule execution.

event_condition defines a logical statement needed to detect spikes. E.g. 'v>30'. It is executed every clock cycle (model time step). When the class is derived from a base class, then the event_condition of the subclass replaces the event_condition of the base class.

after_event_rule the code that is executed when a spike is detected. E.g. 'v=−65;u=u−8;' For a derived subclass, the subclass after_event_rule is executed before the after_event_rule of the base class.

initialization sets the initial values of all variables and parameters of the unit. E.g., 'float v=0; float u=0; float g_AMPA=0;'. Different unit classes may have a different number of synaptic conductances and different variable names. The initialization string parsed by the linker in order to obtain names of all the variables during build. Derived object classes may add new variables. For a derived subclass, the initialization of the base class is executed first, and then this initialization later, as it may change some of the default parameters. The initialization may also change the default parameter values inherited from the base class. By way of example, the initialization string 'float g_NMDA=1; g_AMPA=1' create anew variable g_NMDA and resets the value of the existing variable g_AMPA.

Similarly, junctions and synapses can be described using the same methodology as above.

```
<junction of (junction_class)>
    unit_id1
    unit_id2
    initialization
``` provides a generic definition of a neuronal model class that provides connectivity between pairs of units. The field junction_class refers to the name of the parent object class, for example, "gap_junction" or "dendritic_tree". The class fields are as follows:

unit_id1, unit_id2 specifies the ids of the two connected neuronal units.

initialization

Sets the initial values for the parameters and variables. The class junction_class may be used as the base to define a subclass <junction_class of (junction_class)> and is declared as follows:

```
<junction_class of (junction_class)>
    junction_class_id
    execution_condition
    unit_class_1
    unit_class_2
    update_rule
    initialization
``` where junction_class_id is a unique identification label that specifies the class that can be derived from another class.

execution_condition the condition that is evaluated at every model execution time step in order to determine whether or not to execute units of this class, for example: 'now%10==0'; or 'DA>0.1'. If the execution_condition is absent (the field is blank), then respective unit is executed at every model time step. When a class (subclass) is derived from a base class (superclass), then the derived class execution condition overrides the base class execution condition.

unit_class_1;

the class identifier of the unit_1;

unit_class_2 the class identifier of the unit_2; if omitted, the junction is assumed to be applied to all unit classes.

update_rule defines a code string that will be converted by the linker to executable code. In one example, the code string comprises a forward Euler numerical method notation, such as, for example:

'g_2to1*(V2−V1), g_1to2*(V1−V2)'.

In another example, applicable to Ohmic junctions, one can skip the_class part and just specify the conductances g_2to1 and g_1to2 in the <junction>. When the class is derived from a base class, then the object update_rule of the subclass is executed first, followed by the base class rule, thereby allowing for update of certain variable by the subclass rule execution.

Initialization sets the initial values of variables, if any, used to execute the update_code.

The class synapse is declared as follows:

```
<synapse of (synaptic_class)>
    pre
    post
    delay
    initialization
``` where,

```
            pre
            post
``` are identifiers of the pre-synaptic unit and the post-synaptic unit, respectively.
    delay
specifies the axonal conduction delay value (in simulation time steps)
    initialization
sets the initial parameter and variable values. Similarly to the junction class, synapse class may be derived from abase synapse class is declared as follows:

```
<synaptic_class of (synaptic_class)>
    synaptic_class_id
    initialization
``` where,
    synaptic_class_id
is the unique label that specifies the base class, which is used as a vector identifier in order to refer to individual synapses in background processes (though the order may be scrambled). This class can be derived from another class.
    initialization
sets the initial values of the parameters and variables for each synapse, e.g., 'float w=5; float sd=0; float p=0;'. The class defining a pre-synaptic event rule that accesses synaptic variables and post_unit variables, is declared as follows:

```
<presynaptic_event of (event_rule)>
    synaptic_class
    post_unit_class
``` where,
    synaptic_class
denotes the name of the synaptic class to which this plasticity rule applies. The object event_rule is used to specify actions performed when the pre-synaptic unit fires. The rules of the synaptic_class define the short-term plasticity (STP) and long-term potentiation (LTP) part, of STDP rules for a pre-synaptic neuron (unit).
    post_unit_class
specifies the class of the post-synaptic unit thereby defining the domain of the action of the event_rule thereby providing information that is required by the STDP rule execution (e.g., the class to deliver the post-synaptic potential (PSP) and to access variables such as last_spike). The class postsynaptic_event is declared as follows:

```
<postsynaptic_event of (event_rule)>
    synaptic_class
    post_unit_class
``` where,
    synaptic_class
specifies the name of the synaptic class to which this plasticity rule applies. The object event_rule is used to define a list of actions that are performed with synaptic variables when the post-synaptic unit (as referenced with respect to these synapses) fires, thereby implementing the LTP part of the STDP plasticity rule that is executed whenever the post-synaptic unit fires a spike.
    post_unit_class
specifies the class of the post-synaptic unit thereby defining an action domain for this rule. In one embodiment, this rule is configured to accesses synaptic variables only. The event_rule class may also be derived from a base class as follows:

```
<event_rule of (event_rule)>
    event_rule_id
    rule
    initialization
``` where,
    event_rule_id
is a unique label that specifies the rule class. Generally, the rule class may be derived from another object class event_rule.
    Rule
is a string representation of a code that specifies action performed upon occurrence of an event. By way of example, delivery of the post-synaptic potential (PSP) may be specified as"
    'g+=w' or 'I+=w' or 'g+=g*p'.
Similarly, actions associated with a presynaptic_event may be defined as:
    'p *=STP(now-last_active); w-=LTD(now-last_spike);'
while actions associated with a postsynaptic_event may be defined as:
    'w+=STDP(now-last_active)'
where:
    "last_active" is the time elapsed since a previous occasion when the synapse was active;
    last_spike is the time of the last spike of the post-synaptic unit, and
    'now' is the current time.
In addition, the event_rule class may specify tables, e.g., STDP, LTP, or other biologically motivated tables.
    initialization
sets the initial values of the tables as, for example: 'STDP={ , ... , };' or 'STP={ , ... , };LTD={ ... }'.

```
<background_process>
    execution_condition
``` the condition that is evaluated every simulation time step to determine whether or not to run the process. E.g., 'now%10==0' or 'DA>0.1'. If absent, then the process is run every time step. The name of the unit_class or synaptic_class whose local variables can be accessed. The code below will be run in a loop within the class members with an arbitrary order (possibly in parallel). If absent, it is assumed that the process is run once per 'true' execution_condition, and each unit or synapse can be accessed using the unit or synaptic class name. E.g., the unit class 'exc' contains units exc[i] with possibly unknown order that does not necessarily correspond to the order in which they are listed
    update_rule
the code to be executed, e.g. 'DA *=0.9' or in synaptic_class domain 'w+=DA*sd; sd*=0.995;' or without domain just 'exc[rand( )].I=100;'
    initialization
initialization of global variables, e.g., 'float DA=0'.

The time step of the simulation, and other run-time parameters, can be specified. There are a few global variables that are accessible to everybody, e.g. "now"—the present time.

Classes that differ by a parameter should be declared as a single class and the parameter values should be specified in the instantiations. If there are only few, say, two different values of the parameter, then it may make sense to specify two different classes, each having the parameter hard-wired in the equations.

External Interface

External interface of the END framework describes provision of external sensory input into neuronal network (e.g., the network 100 of FIG. 1) and delivery of outputs (via for example, the pathways 102 of FIG. 1) to external robotic apparatus. END external interface comprises two major logical blocks: Sensory Input block, and Output and Monitoring block, described in detail below.

Sensory Input

This block defines connection of the external input to various units of the network model. By way of example, sensory class for an N-channel (numbered 1 to N) spiking retinal input may be declared as follows:

```
<unit_class>
    unit_class_id = 'retina'
    after_event_rule       // may be empty
```

The above class declaration informs the input driver and the computational engine where the spikes from the retina will go. The structure of the input is further defined using the following declaration of N empty units:

```
<unit>
    unit_id = 'retina(1:N)'
```

In one example, there are no update rules that are required to be executed at every network time step. Hence, the computational engine will not spend computational resources on these empty units. However, whenever the spikes from the input channels declared as 'retina' arrive, the input driver will put the unit index into a spike queue as if it actually fired a spike (this will trigger the after_event_rule execution by the engine, if it is not empty). The synapses from the unit to other units will tell the network what to do with spikes. In the case of retinal input on LGN, the retina units will have 1-3 synapses onto some LGN cells.

If the input channel feeds continuous signals, then the signal will update the variable "I" in each unit every millisecond. In this case, one needs to specify the update rule and the event_condition. Of course, the engine will be executing this code every millisecond.

Output and Monitoring:

The output and monitoring block provides an output interface for the network mode. In one implementation, applicable to motor output from the model, the output block specifies connections between the network units and external motor interface or some other actuators. In one example, the motor interface comprises muscle interface. In another example, the motor interface comprises a motor interface configured to control an external robotic apparatus. A unit 'neck_muscles' comprising an N-channel motor output object for interfacing with, for example, neck muscles is declared using END framework as follows:

```
<unit_class>
    asunit_class_id = 'neck_muscles'
    initialization = 'float I=0;'
```

The above declaration informs the output driver which neurons (units) to monitor for changes in the values of the current I. The respective N empty unit objects are then created as follows:

```
<unit>
    unit_id = 'neck_muscles'
```

During execution of the model, the computational engine ensures that at least some of the motor neurons (units) neck_muscles have non-zero (e.g., positive) synaptic projections to these neurons, so that whenever the motor neurons fire, the variable I within the unit object is set to a positive value. The output driver, therefore, monitors the variable I at every model time step, and resets it to I=0 if needed. As the motor output interface does not require execution of update rules (at each model execution time step), the computational engine spends minimal resources on maintaining the 'neck_muscles' units.

In another implementation, applicable to monitoring neural network execution, the output block specifies connections between the network units and external monitoring interface.

Hardware Accelerations

As described above, certain elements of the neuronal model benefit from computations that are performed by specific hardware blocks (hardware accelerators). By way of example, consider a method update_rule of the unit unit_class that consumes a large portion (e.g., 99%) of the engine computational resources:

```
<unit_class>
    unit_class_id='simple_model'
    update_rule = 'v+=(0.04*v+5).*v+140−u+I; u+= a*(b*v−u);'
    event_condition = 'v>30'
    after_event_rule = 'v=−65;u+=d'
    initialization='float v=−65; float u=0; float a=0.1;
        float b=0.5; float d=8;'
```

Provided the implementation of the update_rule does not change from unit to unit and/or from one model run to another, then computational operations associated with the update_rule can be more efficiently executed by in a specialized hardware accelerator that may be implemented in, for example, an ASIC, FPGA, or specialized silicon. Within the END framework, a 'simple_model' class is used to instruct the compiler to direct execution of the code, associated with, for example, the update_rule listed above to the appropriate location corresponding to the hardware accelerator interface. To create such mappings, instances of the simple_model class are instantiated as follows:

```
<unit of (simple_model)>
    unit_id=509
    initialization 'a=0.01; d=2'
```

Such hardware accelerators (simple_model objects) may be used by the END as building blocks for constructing more complex objects. By way of example, the neuronal model with, for example, one million (1 M) of simple_model units (neurons) and, for example, one thousand (1K) neurons with an extra slow neuronal variable, 'w' may be declared using class inheritance mechanism as follows:

```
<unit_class of (simple_model)>
    unit_class_id='complex_model'
    update_rule = 'w+=0.001*(0.3*v-w); I-=w'
    after_even_rule = 'w+=1'
    initialization='float w=0'
```

A processor in the computational engine (e.g., an ARM chip) that is attached to the specialized hardware will typically process 1K units of the above type in order to evaluate dynamics of the variable 'w' and incorporate it into the value of the variable I. Then the hardware accelerator (analog or digital) hardware may execute 1 M+1K instances of the simple_model without even realizing that some of the instances correspond to a more complex model. Ideally, the specialized hardware will contain the most commonly used implementations of neuronal models, synaptic dynamics, etc., and users are free to mix and match these canonical capabilities or to add to them whatever extra functionality is needed.

Example 1 spnet

The spnet typically comprises N=Ne+Ni=1000 neurons, where Ne=800 excitatory neurons and Ni=200 inhibitory neurons. Each neuron typically comprises M=100 synapses per neuron. All excitatory synapses are plastic (STDP), with a random delay ranging between 1 ms and D=20 ms. The inhibitory→excitatory synapses are non-plastic with a delay of D=1 ms. There are no inh→inh synapses. The low-level END description of the model is expressed as follows. The first Ne units are populated by Ne excitatory units:

```
<unit of (exc)>
    unit_id = 1:800
```

Next, Ni inhibitory units are records of the class are populated as:

```
<unit of (inh)>
    unit_id = 801:1000
```

The spnet class is then declared as shown in the Listing 1 below:

Listing 1.

```
<unit_class>
    unit_class_id='QIF2'
    update_rule = 'v+=0.5*((0.04*v+5).*v+140-u+I);
v+=0.5*((0.04*v+5).*v+140-u+I);'
    event_condition = 'v>30'
    after_event_rule = 'v=-65;'
    initialization = 'float v=-65; float u=0.2*v; float I=0'
<unit_class of (QIF2)>
    unit_class_id='exc'
    update_rule = 'u+=0.02.*(0.2*v-u);'
    after_event_rule = 'u+=8; last_spike=now'
    initialization = 'int last_spike=-1000;'
<unit_class of (QIF2)>
    unit_class_id='inh'
    update_rule = 'u+=0.1.*(0.2*v-u);'
    after_event_rule = 'u+=2;'
    Ne*M records of the class (exc->exc)
<synapse of (GLU)>
    pre = i        // i=1:Ne
    post = j    // a random number between 1 and N
    delay // a random number between 1 and D
    Ni*M records of the class
<synapse of (GABA)>
    pre = i        // i=Ne+1:N
    post = j // a random number between 1 and Ne
<synaptic_class>
    synaptic_class_id = 'GLU'
    initialization = 'float w=6; float sd=0; int last_active=-1000;'
    delay=1 // default delay (if not specified in the instance )
<synaptic_class>
    synaptic_class_id='GABA'
    delay=1 // the same for all synapses
<presynaptic_event of (EPSP_plus_LTD)>
    synaptic_class = 'GLU'
    post_unit_class = 'QIF2'// i.e., exc and inh
<presynaptic_event of (Inhibition)>
    synaptic_class = 'GABA'
    post_unit_class = 'QIF2'// i.e., exc and inh
<postsynaptic_event of (LTP)>
    synaptic_class = 'GLU'
    post_unit_class='exc'
<event_rule>
    event_rule_id = 'EPSP_plus_LTD'
    rule = 'I+=w; sd-=LTD(now-last_spike); last_event=now'
    initialization = 'LTD = {array};'
    // exponential decay from LTP_A=1.2 to zero with LTD_tau=20 ms
<event_rule>
    event_rule_id = 'LTP'
    rule = 'sd+=LTP(now-last_active);'
    initialization = 'LTP = {array};'
<event_rule>
    event_rule_id = 'Inhibition'
    rule = 'I-=5;'
    initialization = ''
<background_process>
    id = 'Weight_update';
    execution_condition = 'now%1000==0'
    domain = 'GLU'
    update_rule = 'w += 0.01+sd; if (w<0) w=0; if (w>10) w=10; sd *= 0.9'
<background_process>
    id = 'randominput'
    update_rule = 'exc[int(floor(rand( )/RAND_MAX*N))].v=30;'
```

Biliary Data Format and Engine Pseudocode

The low-level description of the model (such shown in Listing 1 above) contains only minimal information that is necessary to uniquely define network architecture. The description shown in Listing 1 may not be suitable for, inter alia, performing model simulations, because it does not provide sufficient level of detail, such as, for example, synapse connections for each unit, the pre-synaptic connections, post-synaptic targets, etc. A linker uses (e.g., the linker 108 in FIG.

1) the low-level END description and (i) populates all of the links between the units; (ii) saves the code and the data in binary or some other low-level (machine) format so that to facilitate data and code loading by the computational engine during model simulations. During simulation execution (runtime) the engine may create save-points (that is saving the engine execution state comprising for example, registers and memory content, program counter, etc.) in the same (or a different) format, so to enable a rapid restart of model execution from any save-point.

In one embodiment, the computational engine comprises a single-processor computer. The engine performs a number of computational cycles (steps through the network) in at predetermined time step. In one example, the time step is set to one millisecond.

In certain embodiments, the computational engine may be implemented on a multi-core processing platform, an array of single/multicore processors, an FPGA, or a programmable logic fabric with one or more embedded processor cores.

Typically, every <_class> instance in the low-level END description corresponds to a separate loop execution loop. Computations within each execution loop/cycle may be performed in parallel in an order that is optimized for multi-core implementations. Some cycles may also be performed in parallel with other cycles. Each_code should be "pre-compiled" and included into the appropriate place in the engine.

In order to achieve execution efficiency during model simulations, neuromorphic hardware implementing the computational engine typically has the following features: (i) fast highly specialized processing of neuronal dynamics and basic synaptic events, such as synaptic release; and (ii) a general purpose processor (e.g., an ARM core) for performing of computational background processes, such as slow synaptic update, turnover, rewiring, short-term plasticity, etc. Such configuration enables fast execution of the basic synaptic processing (that less likely requires frequent modifications by the user) for the majority of synapses while allowing for implementation of proprietary boutique processing for a smaller fraction of synapses.

Minimal Instruction Set END Framework

One objective of a "minimal instruction set" embodiment is to provide a low-level description format comprises (i) unit (neuron) definitions, which declare memory allocations but do not contain actions, (ii) junctions, which couple units, but do not allocate memory of their own; and (iii) rules, which link actions with units or junctions. In one example, the actions are clock-driven (that is, executed for the appropriate units at every time step of the neuronal mode simulation execution). In another example, the actions are event-driven, (that is, the actions are triggered by units via, for example, an event_condition declared for the unit class, which informs the simulator on the actions that are performed upon the unit firing a spike. Such events (spike), hence, trigger execution of event-based rules that may be applied to other units or junctions.

Within the END framework a synapse can be declared as a unit comprising memory configured to store various variables associated with synapse functionality, such as synaptic weight, delay, target destination, etc. A synapse can be considered as pre-synaptic machinery that is ready to release transmitter. As with unit updates, synaptic update rules (e.g., maintenance 'w+=sd; sd*=0.9') may be clock-based or event-based. The synaptic action (e.g., release of neurotransmitter) may be triggered by a spike event at the unit corresponding to the pre-synaptic neuron. The rule describing the release can also perform the depression part of the STDP and any of the short-term plasticity processes. The LTP part of STDP may be effected by a separate, other rule that may be triggered by the unit corresponding to the post-synaptic neuron. A junction specifies a connection between a synapse and a post-synaptic unit.

The minimal instruction set example of END enables construction of a simple event-based computer that has enough descriptive capacity to define an arbitrary neural network.

The syntax and structure of the classes and variables of the minimal instruction set example of END, described below, is similar to the END 1.0 format describes supra.

```
<unit of unit_class>
    unit_id
    initialization
<unit_class (of unit_class)>
    unit_class_id
    initialization
<junction of junction_class>
    junction_id
    unit_1
    unit_2
<junction_class (of junction_class)>
    junction_class_id
    unit_class_1
    unit_class_2
<rule of rule_class>
    subject_id
``` the id of a unit or junction that is subject to this rule
trigger_id
the id of the unit that triggers the rule for the subject (for event-based rules). If omitted, this rule is clock-based.
Delay
The delay with which this rule has to be executed. If omitted, there is no delay

```
<rule_class (of rule_class)>
    rule_class_id
    execution_condition
``` e.g. 'now%10==0'. If omitted, then the rule is executed every time step
subject_class
the class to which this rule can be applied. Notice that subject class can be a unit or a junction

```
code
event_condition
initialization
```

Example 2 spnet

Listing 2

```
// First, allocate memory for neurons
<unit_class>
    unit_class_id = 'neuron'
    initialization = 'float v=−65; float u=0; float I=0; int last_spike=−1000;'
```

Listing 2

```
<unit_class of neuron>
    unit_class_id = 'exc'
<unit_class of neuron>
    unit_class_id = 'inh'
<unit of exc>
    unit_id = 1:800
<unit of inh>
    unit_id = 1:200
    // Now, assign dynamics to neurons (clock-based rule)
<rule_class>
    rule_class_id = 'QIF'
    subject_class = 'neuron'
    code = 'v+=0.5*((0.04*v+5).v+140-u+I);
v+=0.5*((0.04*v+5).*v+140-u+I);'
    event_condition = 'v>30'
<rule_class of QIF>
    rule_class_id = 'RS'
    subject_class = 'exc'
    code = 'u+=0.02.*(0.2*v-u):'
<rule of RS>
    subject_id = exc(1:800)
<rule_class of QIF>
    rule_class_id = 'FS'
    subject_class = 'inh'
    code = 'u+=0.1.*(0.2*v-u);'
<rule of FS>
    subject_id=inh(1:200)
    // Specify the after-spike rest (event-based rule)
<rule_class>
    rule_class_id = 'reset'
    code = 'v=-65; last_spike=now;'
<rule_class of reset>
    rule_class_id = 'RS_reset'
    subject_class = 'exc'
    code = 'u+=8;'
<rule of RS_reset>
    subject_id = exc(1:800)
    trigger_id = exc(1:800)
<rule_class of reset>
    rule_class_id = 'FS_reset'
    subject_class = 'inh'
    code = 'u+=2;'
<rule of FS_reset>
    subject_id = inh(1:200)
    trigger_id = inh(1:200)
    //specify synapses.
    // Inhibitory synapses are not plastic.
<rule_class>
    rule_class_id = 'inhibition'
    subject_class = 'neuron'
    rule = 'I-=6'
    // 200*100 records of the form below, each specifying an inh synapse
<rule of inhibition>
    subject_id = {an exc or inh unit}
    trigger_id = {an index of inh unit}
    //Excitatory synapses are plastic, so their weights are stored
<unit_class>
    unit_class_id = 'synapse'
    initialization = 'float w=5; float sd=0; int last_active=-1000;'
<unit of synapse>
    unit_id = 1:80000
    //for each synapse, specify its target. This is done via junctions
<junction_class>
    junction_class_id = 'GLU'
    unit_class_1 = 'synapse'
    unit_class_2 = 'neuron'
    // Assign the synapses, i.e., create 80000 records of the form
<junction of GLU>
    junction_id = 1:80000
    unit_1 = 1:80000
    unit_2 = {random neuron index}
    // Specify which pre-synaptic neurons trigger which synapses
<rule_class>
    rule_class_id = 'EPSP_plus_LTD'
    subject_class = 'GLU'
    code = 'I+=w;sd-=LTD(now-last_spike);last_active=now;'
    initialization = 'LTD={array}'
<rule of EPSP_plus_LTD>
    subject_id = 1:80000
    trigger_id = exc(rand(800))
    delay = rand(20)
    // Specify LTP when post-unit fires
<rule_class>
    rule_class_id = 'LTP'
    subject_class = 'synapse'
    rule = 'sd += LTP(now-last_active)'
    initialization = 'LTP={array}'
<rule of LTP>
    subject_id = 1:80000
    trigger_id = {corresponding post-synaptic neuron, though this could in principle be anything else}
    //perform the sd-update (maintenance)
<rule_class>
    rule_class_id = 'synaptic_maintenance'
    subject_class = 'synapse'
    execution_condition = 'now%1000==0'
    code = 'w += 0.01+sd; if (w<0) w=0; if (w>10) w=10; sd *= 0.9'
<rule of synaptic_maintenance>
    subject_id = 1:80000
    // Finally, the random thalamic input that fires a neuron per ms of time step
<rule_class>
    rule_class_id = 'input'
    code = 'fire({random neuron});'
<rule of input> // no parameters; just need this to instantiate the input
```

END 2.0

The END 2.0 format comprises the following features when compared to the END 1.0 format described, supra.

No inheritance (no object classes);

No background processes (global variables are used instead);

No separate pre-synaptic/post-synaptic rules (all are part of the synaptic type)

Each rule may include other rules and code strings, as well as execution conditions,

```
<rule>
    name
    exec_condition
``` the condition that is evaluated every step to determine whether or not to execute this rule. This can be a string e.g., 'now%10==0' or 'DA>0.1' or a reference to a rule name (this is useful if the condition needs some global tables). If absent, then the rule applies for every execution time step. This condition may access any variable that is defined in the code below.

Code the code string or other rule name that specifies what to do when the rule occurs. E.g., 'I+=w' or 'v+=tau*(2*(v+70)*(v+50)-u+I)/20; u+=tau*0.1*(2*(v+70)-u);'. In addition, the output of the rule can be a logical (true/false) statement that is used in spike conditions, etc. Multiple rule names can be provided here; they will be executed in the provided order init declares and sets the values of global variables used in this rule. E.g. 'STDP={ , ... , }; DA=0' or 'STP={ , ... , }; LTD= { ... }'. Any instance variables are defined in unit_type and synaptic_type; the linker checks that all data types defined in different unit_types and synaptic_types are consistent with respect to the rule.

```
<unit_type>
    name
    update_rule
``` code string or rule name that is executed every time step. Multiple rules can be provided here; they will be executed in the order specified.

event_condition logical statement or rule name needed to detect spikes. E.g. 'v>30'. Executed every time step event_rule the code or rule name that is executed when a spike is detected. E.g. 'v=−65;u=u−8;'

Init declares and sets the initial values of all variables and parameters used in the unit (i.e., instance variables). The linker (compiler) checks that these variables have consistent data types among all unit types that use the same rules, for example, 'analog v=0; analog g_AMPA=0;'

```
<unit of unit_type>
    unit_id
    init
``` sets the parameter and variable values that are different from the default values in the definition of the type. All these have to be declared and already initialized with default values in the definitions of unit_type

```
<junction_type>
    name
    update_rule
    init
    <junction of junction_type>
    unit_1
    unit_2
    init
    <synaptic_type>
    type
    presynaptic_event_rule
``` the code or rule name that is triggered when the pre-synaptic neuron fires. This takes care of LTP and PSP postsynaptic_event_rule the code or rule name triggered by firing of the post-synaptic unit. This takes care of the LTD part of STDP update_rule Code string or rule name that is executed every time step (hopefully, it has execution_condition and is hence executed rarely). Multiple rules can be provided here; they will be executed in the order specified. This is needed for synaptic maintenance, in lieu of background processes.

```
<synapse of synaptic_type>
    pre
    post
    delay
    init
    <global_variable>
    update_rule
```

Rule name that initializes global variables and executes the code that updates them. The code may have access to specific instances of units, junctions, or synapses. In the simplest case, the rule can be just an assignment of the value of the global variable based on a value of an instance.

Notice that instance variables are used in <rules> but they are defined in <unit_type>, <junction_type>, and <synaptic_type>. It is assumed that all declaration of instance variables are consistent with all the rules. There may be two problems: Situations where a variable is used in a rule but is not defined in unit_type or junction_type or synaptic_type are handled as follows:

The linker may generate an error

The linker uses a default type of the variable, e.g., "analog"

The linker is instructed to look at other usage of the rule and if the variable is defined somewhere, it extends its definition.

In certain embodiments, a variable can be defined differently in two or more unit_types that use the same rule. Again, there are multiple possible solutions to this:

The linker generates an error

The linker converts one of the definitions to the other one. For example, there can be a partially ordered set of definitions, e.g., int8<int16<int32<int64< analog, so that two definitions are transformed to the common one The linker splits the rule into two rules, rule_a and rule_b, that act on different types of variables Example 2

Global Variables

```
<rule>
name = 'DA_update'
code = 'DA = exc[3].v + inh[1].u'
init = 'analog DA = 0'
<global_variable>
update_rule = 'DA_update'
```

Example 3 spnet

The standard spnet network has N=1000 neurons; among them are Ne=800 excitatory neurons and Ni=200 inhibitory neurons, with M=100 synapses per neuron. All excitatory synapses are plastic (STDP), with random delay between 1 and D=20 ms. The inhibitory→excitatory synapses are non-plastic with delay D=1 ms. There are no inh→inh synapses. The low-level description of the model is below.

```
<rule>
name='QIF2' // only the v equation defined
code = 'v+=(0.04*v+5).*v+140+I; I=4*rand( )/MAX_RAND'
<rule>
name='spike'
code = 'v>30'
<unit_type>
name = 'exc'
update_rule = 'u+=0.02*(0.2*v−u); I−=u;'
update_rule = 'QIF2'
event_condition = 'spike'
after_event_rule = 'v=−65; u+=8; last_spike=now'
init = 'analog v=−70, u=−14, I=0; int last_spike=−1000'
```

```
<unit_type>
name='inh' // inhibitory neuron
update_rule = 'u+=0.1.*(0.2*v-u); I-=u;'
update_rule = 'QIF2'
event_condition = 'spike'
after_event_rule = 'v=-65; u+=2;'
init = 'analog v=-70, u=-14, I=0; int last_spike=-1000'
//Ne records of the class
<unit of exc>
unit_id = 1:800 // i=1:Ne
//Ni records of the class
<unit of inh>
unit_id = 1:200 // i=1:Ni
<rule>
name = 'EPSP_plus_LTD'
code = 'I+=w; sd-=LTD(now-last_spike); last_active=now'
init = 'LTD = {array};'
<rule>
name = 'LTP'
code = 'sd+=LTP(now-last_active);'
init = 'LTP = {array};'
<rule>
name = 'Synaptic_Maintenance'
execution_condition = 'now%1000==0'
update_rule = 'w += 0.01+sd; if (w<0) w=0; if (w>10) w=10; sd *= 0.9'
<synaptic_type>
name = 'GLU'
presynaptic_event_rule = 'EPSP_plus_LTD'
postsynaptic_event_rule = 'LTP'
update_rule = 'Synaptic_Maintenance'
init = 'analog w=6, sd=0; int last_active=-1000;'
<synaptic_type>
name='GABA'
presynaptic_event_rule = 'I-=5'
delay=1 // Default delay; the same for all synapses
//Ne*M records of the class (exc-> exc or inh)
<synapse of GLU>
pre = exc[i]// i=1:Ne
post = exc[j] or inh[j] // random, between 1 and Ne or 1:Ni
delay // a random number between 1 and D
//Ni*M records of the class (inh->exc)
<synapse of GABA>
pre = inh[i]// i=1:Ni
post = exc[j] // a random number between 1 and Ne
```

END 3.0

The END format 3.0 implements several major changes when compared to the END 2.0 format. These include:

Introduction of one-way junctions

Splitting of the junction update_rule into two rules: the update_rule (configured to modify junction variables); and the delivery_rule (to configured modify the post-synaptic unit variables)

Removal of the postsynaptic_event_rule

Splitting of the presynaptic_event_rule into: the prepost_rule (for LTP part of STDP); the postpre_rule (for LTD part of STDP); and the delivery_rule (for delivering PSP)

Atomic addition for the delivery_rule (for junctions and synapses)

Removal of the clock-based synaptic update rule (it can be implemented via postpre_rule)

Implementing global variables via links to instance variables.

All names and statements in END 3.0 have similar meaning to those in END 2.0 unless stated otherwise. For END 3.0, the syntax exc:3 is used to refer to the instance 3 of the type 'exc'.

Synaptic Rules

The presynaptic_event_rule can comprise multiple independent rules. For the purposes of this description, the designators t1 and t2 denote the times of spikes of the pre-synaptic neuron arriving at the post-synaptic unit (i.e., conduction delay is already incorporated into t1 and t2), where the t2 corresponds to the current simulation time (also referred to as 'now').

The prepost_rule may be executed at any time before t1 to implement the LTP part of STDP that would correspond to a pair of pulses with pre-synaptic neuron firing at t1 and a subsequent post-synaptic neuron firing after t1 but before or at t2. While the prepost_rule rule has access to the system variables prepre (now—t1) and prepost (post_spike-t1), it does not have access to any post unit variables or the system variable at time t2 ('now'), as it is not clear when this rule is called. If prepost_mode=11 (1-to-1), then each pre-synaptic spike triggers only 1 call for prepost_rule. If prepost_mode=1A (1-to-all), then each pre-synaptic spike triggers prepost_rule for all subsequent post-synaptic spikes (with its own prepost variable), up to the moment of the next pre-synaptic spike. The parameter prepost_max (if given) further limits the span of time after the pre-synaptic spike during which to consider post-synaptic spikes for prepost_rule. For example, if the LTP window of STDP is only 50, then there is no point of considering pairs of pre-post spikes with the interval greater than 50. In another embodiment, prepost_rule may be called when the earliest post spike after t1 occurs later than t1+prepost_max. In certain embodiments, the rule is not called if the post spike never occurs during the period between t1 and t2.

The postpre_rule is typically executed just before time t1 in order to update the synaptic variables based on the timing of the previous pre-synaptic spike (prepre=t2-t1) and the last post_synaptic spike (postpre). The latter variable is typically provided even if a long period of time has elapsed since the previous post spike occurred. The variable 'now' points to the current time, and all variables from the post-synaptic unit are available for reading.

The delivery_rule is typically called at time t1, but after the postpre_rule updated the synaptic weights. The delivery_rule has access to all the variables of the latter rule, plus has write access for atomic addition to the variables of the post unit.

Listing 3

```
<rule>
    name
    exec_condition
    code
    init
<unit_type>
    name
    update_rule
    event_condition
    after_event_rule
    init
<unit of unit_type>
    unit_id
    init
<junction_type>
    name
    update_rule
    delivery_rule
    init
<junction of junction_type>
    pre
    post
    init
<synaptic_type>
    type
    prepost_rule
```

In the code example shown in Listing 3, the rule is triggered before t2 and it modifies the synapse. The rule can read and write synaptic variables but does not have access to any variables from the post-synaptic unit. The rule has access to prepre=t2−t1 and prepost (post spike−t1).

prepost_mode

Two modes are supported, 11 (1-to-1) and 1A (1-to-all). The former calls the rule at most once, while the latter calls multiple times for each post unit spike after the pre unit last spike. Default: 11 prepost_max limits the scope of time after the pre unit spike to consider to form pre-post pairs. All post spikes after t1+prepost_max will be ignored.

postpre_rule the code or rule name that is triggered at t2 and modifies the synapse. It can read and write synaptic variables and has read access to variables from the post-synaptic unit. It has access to prepre, postpre, and now=t2.

delivery_rule the code or rule name that is triggered at t2 and modifies variables of the post unit. It has read access to synaptic variables, prepre, postpre, and now=t2. This code is atomic addition.

```
<synapse of synaptic_type>
    pre
    post
    delay
    init
```

Identifying Event-Triggered Pre-Unit Variables

In certain embodiments, it can be desirable to model short-term synaptic plasticity, which is triggered by pre-synaptic spikes. Often, this requires having a variable or a vector of variables that is modified by each pre-synaptic spike and then evolves according to some equation, but only values of this variable at the moment of pre-pulses are needed. In this case, the variable may be part of each synapse. However, since the value of all such variables is the same for all synapses, a compiler (linker) from END to an engine can remove these variables from synapses and use a single pre-synaptic variable instead, subject to a "pre-rule". Alternatively, the END format may have a special tag or a label, or a statement that would help the compiler to identify such pre-event triggered variables in synaptic event rules or pre-synaptic unit event rules.

If the END program is distributed among multiple engines, then each engine can transfer the value of such variables with each pre-synaptic spike. Alternatively, each engine that receives synapses from such pre-synaptic unit can keep a local copy of the variable, updating it the same way as it is updated in the engine that hosts the pre-synaptic unit.

Example 4 spnet

The spnet network typically comprises N=Ne+Ni=1000 neurons, where Ne=800 excitatory neurons and Ni=200 inhibitory neurons. Each neuron typically comprises M=100 synapses per neuron. All excitatory synapses are plastic (STDP), with a random delay ranging between 1 ms and D=20 ms. The inhibitory→excitatory synapses are non-plastic with a delay of D=1 ms. There are no inh→inh synapses. The low-level END 3.0 description of the model is expressed as follows.

| Listing 4 |
| --- |

```
<rule>
    name='QIF2' // only the v equation defined
    code = 'v+=(0.04*v+5).*v+140+I; I=4*rand( )/MAX_RAND'
<rule>
    name='spike'
    code = 'v>30'
<unit_type>
    name = 'exc'
    update_rule = 'u+=0.02*(0.2*v−u); I−=u;'
    update_rule = 'QIF2'
    event_condition = 'spike'
    after_event_rule = 'v=−65; u+=8;'
    init = 'analog v=−70, u=−14, I=0;'
<unit_type>
    name='inh' // inhibitory neuron
    update_rule = 'u+=0.1.*(0.2*v−u); I−=u;'
    update_rule = 'QIF2'
    event_condition = 'spike'
    after_event_rule = 'v=−65; u+=2;'
    init = 'analog v=−70, u=−14, I=0;'
    //Ne records of the class
<unit of exc>unit_id = i // i=1:Ne
    //Ni records of the class
<unit of inh>
    unit_id = i // i=1:Ni
<rule>
    name = 'LTD'
    code = 'sd−=LTD(postpre); w += 0.00001*prepre + sd*10*(1−
0.9999^prepre); if (w<0) w=0; if (w>10) w=10; sd *= 0.9999^prepre)'
    init = 'LTD = {array};'
    // sd'=−sd/10 sec; 0.9999^x = exp(−x/10000); the rule could be
optimized so that 0.9999^x is computed only once: w+10*sd; sd*=..;
w−=10*sd;' It could be further optimized so that 10* is removed (but
LTP and LTD tables are scaled up by 10).
<rule>
    name = 'LTP'
    code = 'sd+=LTP(prepost);'
    init = 'LTP = {array};'
<synaptic_type>
    name = 'GLU'
    prepost_rule = 'LTP'
    postpre_rule = 'LTD'
    delivery_rule = 'I+=w'
    init = 'analog w=6, sd=0;'
<synaptic_type>
    name='GABA'
    delivery_rule = 'I−=5'
    delay=1 // Default delay; the same for all synapses
    //Ne*M records of the class (exc−> exc or inh)
<synapse of GLU>
    pre = exc:i// i=1:Ne
    post = exc:j or inh:j // random, between 1 and Ne or 1:Ni
    delay // a random number between 1 and D
    //Ni*M records of the class (inh−>exc)
<synapse of GABA>
    pre = inh:i// i=1:Ni
    post = exc:j // a random number between 1 and Ne
```

Event-Driven Architecture

An Event Driven Architecture (EDA) may be defined as a generalization of the END format that acts as an abstraction layer configured to isolate computational description from the neuroscience description of the model. The EDA defines memory management, parallelism, and rules triggered by events and enables compilation of the END-code directly into EDA code.

The events in END format and EDA architecture correspond to pulses, whether physical or virtual, software representation of pulses, stereotypical bursts of pulses, or other discrete temporal events.

EDA Memory Management

EDA memory management differs (from the point of view of ownership of variables) from the END framework in the following:

Units own their own variables. When an update rule for a unit A is executed, it does not require access to variables of any other units of the network. Conversely, no rules being executed by other units require access to the variables of the unit A.

Synapses own their own "synaptic" variables, such as weights, variables such as last_active, etc., and they may refer to (read from and write to) certain variables in the post-synaptic unit. When either presynaptic_rule or postsynaptic_rule is executed, two or more synapses may try to access and modify the same variable of the post-synaptic unit. However, the synapses do not compete for their own synaptic variables.

Junctions own their "junction" variables, but they access and modify variables in the unit_1 and unit_2. When junctions are executed, there is no competition for parallel access to their junction variables, but there may be competition for the access to unit_1 and unit_2 variables.

Thus, units, synapses, and junctions may be treated as units, doublets, and triplets in terms of ownership of variables. Units own a set of variables, synapses own one set of variables and refer to another set owned by units. Junctions own one set of variables and refer to two other sets of variables owned by two units. This nomenclature can be applied to describe the END 1.0, 2.0 and 3.0 formats, as well as exemplary embodiments below.

Rules and Events

The class member Event_condition triggers execution of the following rules:

After_event_rule that acts on the unit that has triggered the event (the trigger unit);
presynaptic_event_rule that acts on synapses (doublets) that point from the trigger unit to other units;
postsynaptic_event_rule that acts on synapses (doublets) that point to the unit from other units The class member Update_rule is executed at every time step of the network simulation and it updates variables in units, synapses (possibly via a background process), and junctions, i.e., in units, doublets, and triplets.

Units, doublets, and triplets as elements may be referred to as the network elements. The END format, therefore, defines (i) elements, (ii) rules that act on elements, and (iii) events that are triggered by elements and cause execution of other rules that act on other (target) elements.

Definition of EDA Instruction Set

The objectives behind the development of the EDA framework according to certain aspects of the present invention include:

elements (units, doublets, triplets, etc.) that have their own variables and in addition may refer to variables in other elements;
clock-driven rules (rules) that act on variables in elements; and
event-driven rules (events) that are triggered by some elements and act on variables in other (target) elements.

The EDA instruction set starts with defining rules that act on abstract (symbolic) variables. Rules may include other rules defined earlier, so as to form a directed graph of rules with no cycles. Elements are defined by the clock-driven rules that act on the same or other elements. Events are defined by trigger condition and target rule that are applied to other elements.

One example of an EDA instruction set is shown below in Listing 5. Bold keywords in Listing 5 denote components of the END instruction set, whereas non-bold words denote user-defined names and values.

---
Listing 5
---
```
rule_name = rule
    code = '....'
    code = another_rule_name
    init = '....'
```
---

In Listing 5, the identifier "code" can refer to any string of code, or the name of another rule defined previously. While C-code syntax is used in the Listing 5, it will be appreciated by those skilled in the arts that any other language description (including, for example, C#, Python, Perl, etc.) is equally applicable to the invention. There may be multiple codes and rules included within a rule that can be executed in the order of inclusion. In certain embodiments, rules that are used in multiple element types can be defined separately, so that the engine can use its acceleration tricks to execute such rules in parallel. The statement "init" defines static (global within the rule) variables needed to execute the rule, e.g., it defines lookup tables. The "code" may refer to the static variables defined in "init", to instance variables defined in the element (see below) or to other instance variables defined in other element types, e.g., "I+=A.w+B.w" refers to an instance variable I, and to variables w defined in an elements A and B, ---
```
element_name = element
    rule = rule_name
    rank = a number or range of numbers
    init = '....'
```
---

The latter is a definition of an element type. Here, "rule" refers to a rule defined earlier or to a string of code. The parameter "rank" specifies the rank order of execution of the rule within a clock cycle. It takes fixed-point value from the interval [0 1]. E.g., rank=0.45 means that this rule will be executed after all rules with lower rank and before all rules with higher rank, but in parallel with the rules that have the rank 0.45. If rank is given as an interval, e.g., rank=min:max, then the engine has the freedom of executing this rule any time after all rules with rank <min and before all rules with rank>max. If "rank" is missing, it is equivalent to the default value rank=0:1, i.e., the engine has complete freedom of selecting when to execute this rule. If the rank is greater than 1, then the engine skips cycles to execute the rule. For example, rank=2.45 will cause the engine to skip 2 cycles until next execution of the rule. The string "init" defines the names of instance (local) variables of the element and sets their default initial values.

---
```
id = element_name
    A = other_element_name.id
    B = other_element_name.id
    variable_name = value
```
---

The latter is a definition of an instance of the element type. Here, "element_name" is the name of an element type defined earlier. The lines "variable_name=value" may set values of instance variables that are different from the default values defined in the "init" statement in the element definition. If the rule_name in the element definition refers to other elements (which is the case for doublets and triplets), then the ids of these elements must be specified here. Notice that one can use any variable name, not necessarily A and B (or Unit_1 and Unit_2 in END), to refer to other elements.

```
event_name = event
trigger_condition = rule_name
trigger_rank = number or number range
target_code = rule_name
target_rank = number or number range
```

The latter is a definition of an event type. Here, "trigger_condition" is a name of a rule or a string code that returns true/false value. This condition (applied to elements; see below) is evaluated at the rank given by "trigger_rank". When the condition is true, it triggers execution of the "target_code" in the target element (defined below) at the rank "target_rank".

```
event_name
trigger = element_name.id
target = element_name.id
```

The latter is a definition of an instance of the event type. It specifies which element is the "trigger" and which element is the "target" of the event.

Example 3 spnet with No Delays

A network of randomly connected 800 excitatory and 200 inhibitory neurons (100 of exc→all and inh→exc connections) can be defined with excitatory synapses subject to STDP and no conduction delays (for conduction delays, see next example).

Listing 6

```
QIF = rule
    code = 'v+=0.5f*((0.04f*v+5.0f)*v+140.0f−u+I);
v+=0.5f*((0.04f*v+5.0f)*v+140.0f−u+I); I=0.0f;'
exc = element
    code = 'u+=0.02f*(0.2f*v−u);'
    code = QIF
    rank = 0
    init = 'float v=−65.0f; float u=−13.0f; float I=0.0f; int
last_spike=−1000'
    1:800 = exc
inh = element
    code = 'u+=0.01f*(0.2f*v−u);'
    code = QIF
    rank = 0
    init = 'float v=−65.0f; float u=−13.0f; float I=0.0f; int
last_spike=−1000;'
    1:200 = inh
spike = rule
    code = 'v>30'
after_spike_reset_exc = event
    trigger_condition = spike
    trigger_rank = 0.1
    target_rule = 'u+=8; last_spike=now'
    target_rank = 0.2
after_spike_reset_exc
    trigger = exc.1:800
```

-continued

Listing 6

```
    target = exc.1:800
after_spike_reset_inh = event
    trigger_condition = spike
    trigger_rank = 0.1
    target_rule = 'u+=2; last_spike=now'
    target_rank = 0.2
after_spike_reset_inh
    trigger = inh.1:200
    target = inh.1:200
inh_syn_event = event
    trigger_condition = spike
    trigger_rank = 0.1
    target_rule = 'I−=5.0f'
    target_rank = 0.3
// make 200*100 such entries
inh_syn_event
    trigger = inh.<random number between 1 and 200>
    target = exc.<random number between 1 and 800>
weight_update = rule
    code = 'w += 0.01f + sd; if (w<0.0f) w=0.0f; if (w>10.0f)
w=10.0f; sd *= 0.9f'
exc_synapse = element
    code = weight_update
    rank = 999:1000// any time within that cycle
    init = 'float w=6.0f; float sd = 0.0f; int last_active = −1000'
    id = exc_synapse
    post = <either exc.id or inh.id with id = random>
    PSP_LTD_rule = rule
    code = 'post.I += w; sd −= LTD(now − post.last_spike);
last_active = now'
    init = 'float LTD = {...}'
PSP_LTD_event = event
    trigger_condition = spike
    trigger_rank = 0.1
    target_rule = PSP_LTD_rule
    target_rank = 0.3
PSP_LTD_event
    trigger = exc.<each id>
    target = exc_synapse.<each corresponding id>
LTP_rule = rule
    code = 'sd += LTP(now−last_active)'
    init = 'float LTP = {...}'
LTP_event = event
    trigger_condition = spike
    trigger_rank = 0.1
    target_rule = LTP_rule
    target_rank = 0.4
LTP_event
    trigger = {for each exc.id and inh.id}
    target = exc_synapse.<each corresponding id>
```

The linker is typically configured to group all events triggered by 'spike' rule (that are within with the same rank) into a single event, so that the computational engine executes the 'spike' condition only once per model simulation step for each unit.

In certain embodiments, the rank information in provided in the definition of the rule; this way, there is no need to repeat ranks in the definition of events.

Elementary Network Interface

Elementary network interface (ENI) can be implemented as a communication protocol that implements data exchange between two simulations described in the low level description END format or any other entity that is required to send/receive data to/from a simulation (e.g. input device, visualization/debug tool etc.). The ENI is strongly entwined with END itself, and it can be used to partition large END files into smaller pieces, ensuring correct results. Therefore, certain parts of ENI require detailed knowledge of the END engine handling of communication events.

Figure 3:
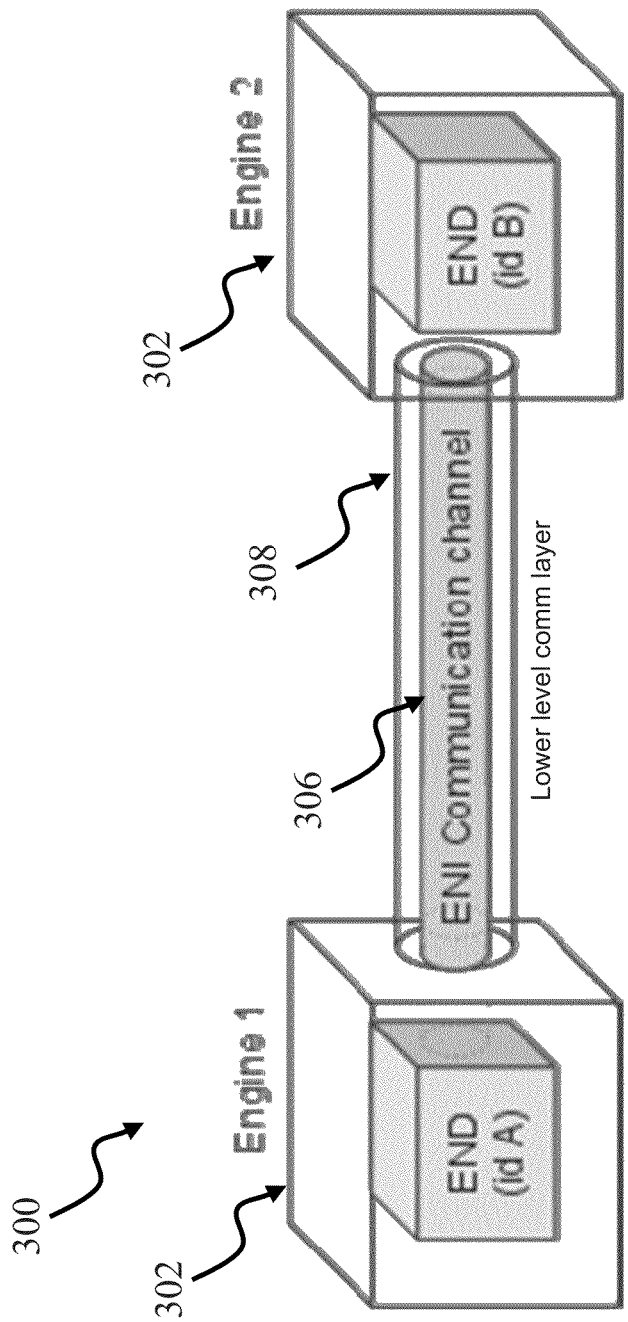
FIG. 3 is a block diagram illustrating one embodiment of END simulations comprising ENI communications channel according to the invention.

Referring now to FIG. 3, a generalized communication framework 300 between two computational engines 302 (each running an END model simulation) is shown and described. The ENI communication protocol is implemented in some physical means of communication (e.g. USB/Bluetooth for peripherals or Ethernet/Infiniband, for more demanding situations). Each computational engine 302 is required to implement the ENI (the communications pipe denoted as 306 in FIG. 3) on top of the transport layers available (the communications pipe denoted as 308 in FIG. 3). Note that ENI forms a layer of communication between models described by END, and not between the engines 302 themselves.

In certain embodiments, the engines 302 are connected by the low level transport layer may discover each other and pair automatically. Manual setup is also possible (e.g. for engines connected via IP protocol). The communication specification file (ENI file) is supplied along with the END file to the engine. Once the engine discovers that it is paired with another engine that runs the right END file, the ENI channel is negotiated and established (green pipe in FIG. 1). The ENI communication specification file can be regarded as a mapping, which helps both parties to understand each other and target the right units of the right classes.

2. ENI Channels

Figure 4:
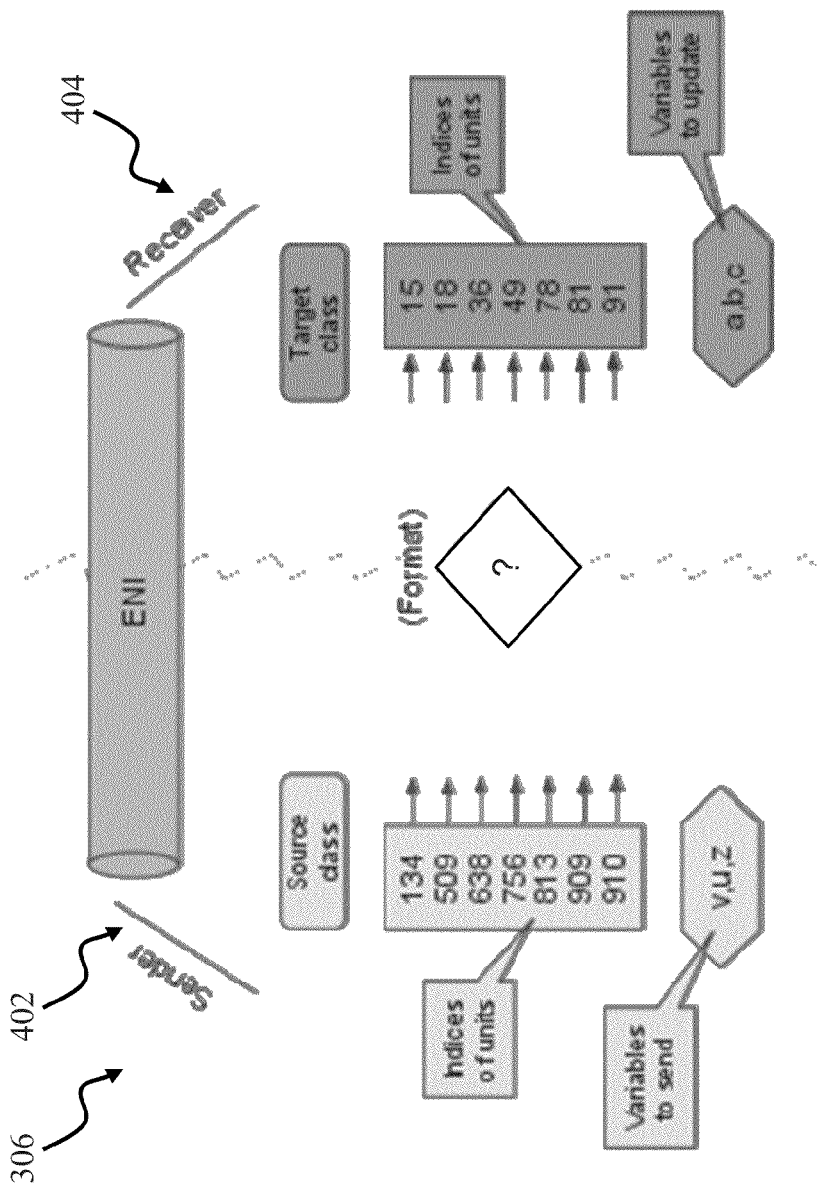
FIG. 4 is a block diagram illustrating one embodiment of ENI communications channel of the invention.

FIG. 4 shows a block diagram of ENI communications channel 306 of FIG. 3. The channel 306 is defined by its endpoints (the IDs of the low level END description, such as the END A and END B in FIG. 3) and a set of parameters that describes how the communication is performed and what type of information is communicated. The communication channel 306 is unidirectional, going from left to right direction, and is defined by the sending entity 402 and the receiving entity 404. The data transfer is one way (though negotiation and meta information in the transport layer are not restricted).

Typically, the ENI channel parameters include:
Sender and receiver END ID's and an identifier that uniquely identifies the channel
Sender and receiver classes
Sender and receiver class instances (enumerated by their number within the class)
Content: events/spike notifications or values of certain parameters
Format of the data sent
Modes of operation (sync, async) and their parameters (frequency, phase shift etc.)

2.1 Content and Format

In one implementation, the ENI communication channel is be used to exchange (i) spike (event) notifications and (ii) values of selected class parameters (variables). These two content types require different data sent through the channel, namely:

Unit indices (for spike notifications)
The actual values of variables (of all instances transmitted by the channel)

In one implementation, network unit indices interleaved with values variables. Such implementation is applicable when the values need to be sent only for the units that experienced an event (spike), so as to minimize network traffic. To summarize, the following data formats are supported:

Indices (some units) either with values or not. If the values are missing, then the data is interpreted as a spike notification.
No indices (all units) but only values. (If the values are missing then the data is interpreted as a spike notification of all the units involved; this is an unlikely case, left for consistency).

Typically, these two content types (i.e., events and data) are not mixed in a single ENI channel instance. In certain embodiments, whenever the ENI channel is set to transmit events/spike notifications, the target units are ("artificially") fired; that is, the event is scheduled on the receivers spike queue but any post event actions like LTP or reset are not performed. In one example, the units that can be fired externally do not have any local incoming synapses that are subject to plasticity rules (e.g., LTP). In another example, the units are configured to respond to both the external firing triggers and plasticity rules such that whenever they are fired externally, the post event rues are not invoked. Such configuration ensures simulation consistency and enables split-simulations produce the same outcome as a "single simulation". Therefore, when partitioned appropriately, it is always (considering the restrictions above) possible to obtain the same results with the splits simulations as with the single simulation. In one example, the model partitioning is facilitated via an introduction of special fake/receiving units as required.

FIG. 4 illustrates content, formats and expected behavior in the ENI communications channel. In the case of transmitting values of variables, the channel description specifies the set of variables of the sender and receiver classes. In other words, ENI specifies which variables within the source class will be mapped to which variables in the target class. The consistency requirement is that either the internal representation of the variables sent through the channel are compatible between sender and receiver or the communication channel performs all necessary conversions. After each communication event, the values in the target class are updated to the new values.

In certain embodiments, the ENI channel transmits data related to units in END format. In certain embodiments, the data related to synapses or junctions (e.g., synaptic weights or other variables) are transmitted.

2.2 Mapping of Units

The ENI channel can introduce a mapping from certain elements of the source unit class in the END format to certain elements of the target class. Each channel establishes communication between one sender class and one receiver class. The mapping establishes the indices that will be sent through the wire (refer to the FIG. 4), if spike notifications are being sent, or the order of values if parameter values are communicated.

2.3 Sending/Receiving Frequency

The ENI channel need not send information at every model simulation cycle. The ENI files specify the periods T1, T2 (expressed in engine model simulations cycles) of sending/receiving. The designator T1 corresponds to the sending side period (so the data will be sent only every T1 cycles), T2 describes the receiver side (data is expected to have been delivered to the simulation every T2 cycles). The data may be delivered to the engine at any point, but the engine will keep (buffer) it and will make it available to the running simulation at the appropriate receiving point.

3. Modes of Operation

The ENI communication channel is typically configurable to operate in two modes—synchronous and asynchronous. In synchronous mode, the transmission and delivery is synchronized to the nearest simulation cycle. In asynchronous mode, the (input) data are continuously provided to the computational engine and delivered to the respective units of the simulation instance whenever it is ready. While the synchronous mode ensures timely delivery of data it may cause serious performance bottlenecks for high input data rates. Conversely, the non-synchronous mode may cause undefined model behavior due to variable data delivery times.

Figure 5:
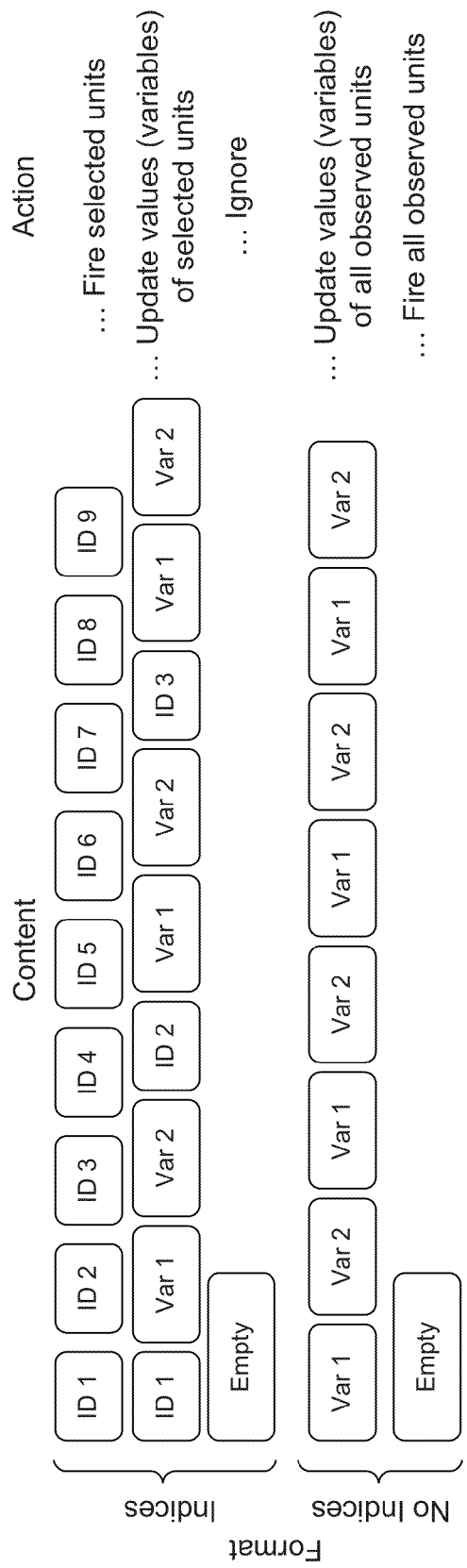
FIG. 5 is a block diagram detailing content, formats and expected behavior in ENI, according to one embodiment of the invention.
Figure 6:
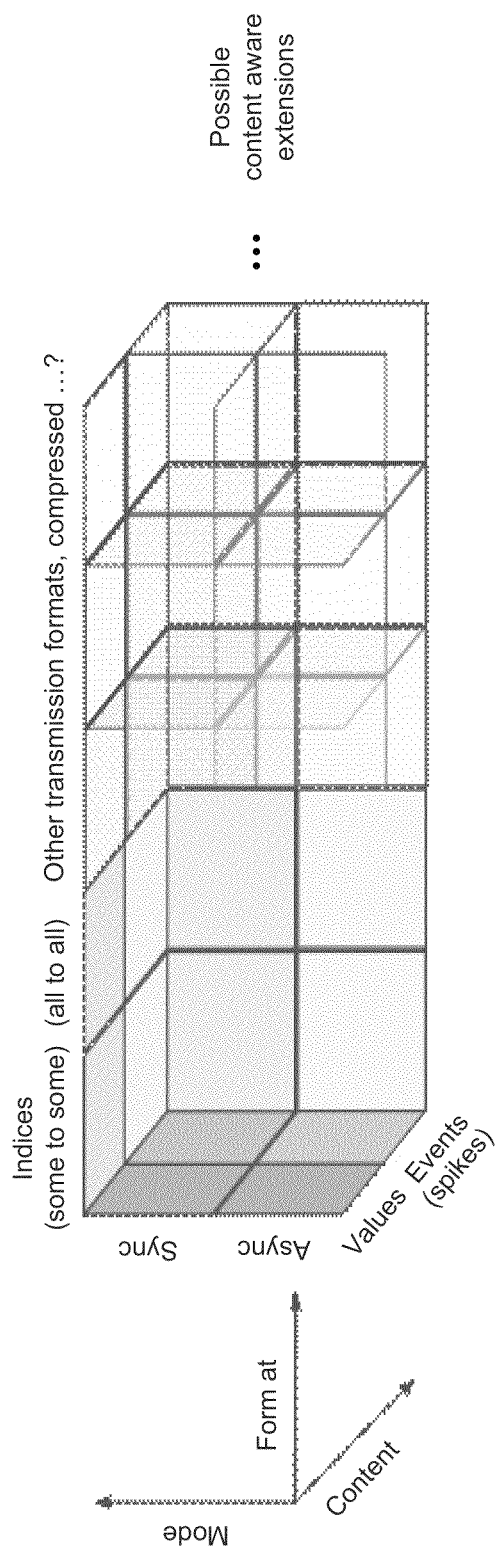
FIG. 6 is a graphical illustration depicting modes of operation of the ENI (scheme) according to one embodiment of the invention.

FIG. 5 presents examples of modes of operation of the ENI (scheme). Combined two formats, two content types and two modes of operation form a cube as illustrated in the embodiment FIG. 6. In certain embodiments, the ENI is extended in terms of possible data formats and in the future may include content aware compression etc.

3.1 Synchronous Mode

In one implementation of the synchronous mode, it is assumed that the receiving engine cannot proceed through the data receiving point unless the necessary data has arrived (so the receiver synchronizes with the sender). The channel in that mode specifies additional property—namely the phase shift S. If the shift S>0 the engine will proceed with the simulation if the data packet sent S cycles ago has arrived (since engines are synchronized it does not matter whether these are sender or receiver cycles). The phase shift allows for better utilization of the communication channel whenever the actual structure of neuro-simulation allows for it (that is certain projections sent through ENI channel have delays that can be used to relax requirements for the channel and introduce the shift, see FIGS. 7 and 7A). The underlying transport may introduce priorities to channels based on their phase shift (the time required to deliver the data).

The sender can proceed with other tasks after the data is sent without waiting for any delivery notification, however if the message is not delivered, the next attempt to send data over the channel will hold the simulation. (The sending engine will not proceed if more than S non-confirmed deliveries occur in a synchronous channel with phase shift S).

3.2 Asynchronous Mode

In certain embodiments, particularly where applicable to the non-synchronous (i.e., asynchronous) mode, the frequency of sending and receiving data is specified, but the engine does not stop its execution until the data are sent. On the receiving side, the asynchronous mode does not impose any data delivery timing restrictions. In one example, the computational engine is configured to receive the data arriving in indivisible chunks (block transfer). In another example, the data are transferred via a stream (streaming transfer). Other examples are possible, such as, for example, a combination of block and streamed transfer. In the block transfer sub-mode, the transmitted message is assumed to be delivered only after all the data within the block has been delivered to the receiver (e.g., the receiver 404 in FIG. 4) and the communication transaction is completed. In the streaming sub-mode, the data that becomes available at the receiver is gradually transmitted to the engine, regardless of whether the transmission transaction has completed or not.

In the asynchronous block mode it may be assumed that only the latest message is actually delivered to the engine, while others received before the engine encountered the receiving point are discarded (It might be useful when a real-time input device (like a camera) is sending data in non synchronous mode faster than the engine can handle). The asynchronous streaming mode accumulates all the data, and delivers it at the closest receiving point.

Figure 7A:
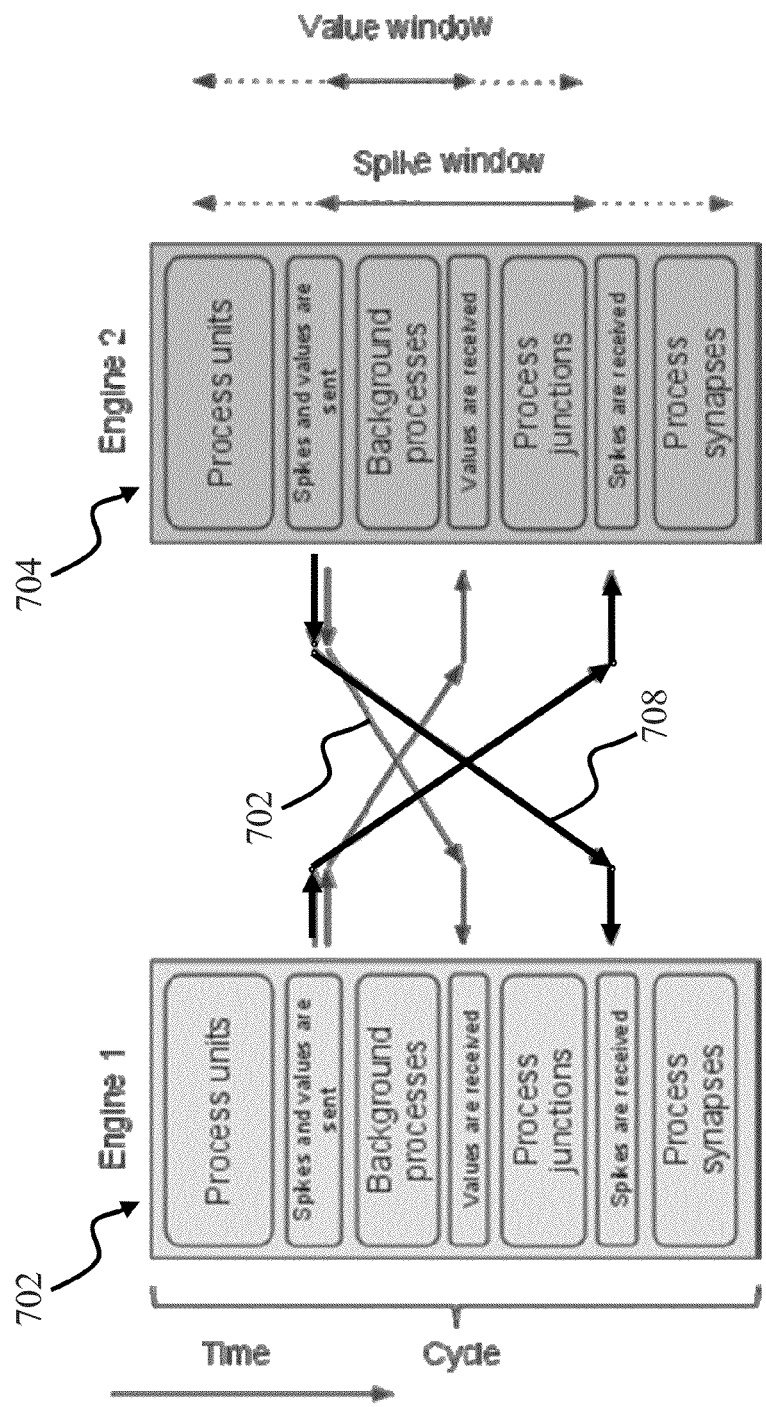
FIG. 7A is a block diagram illustrating one embodiment of a fully synchronous communication over the ENI channel, according to one embodiment of the invention.
Figure 7B:
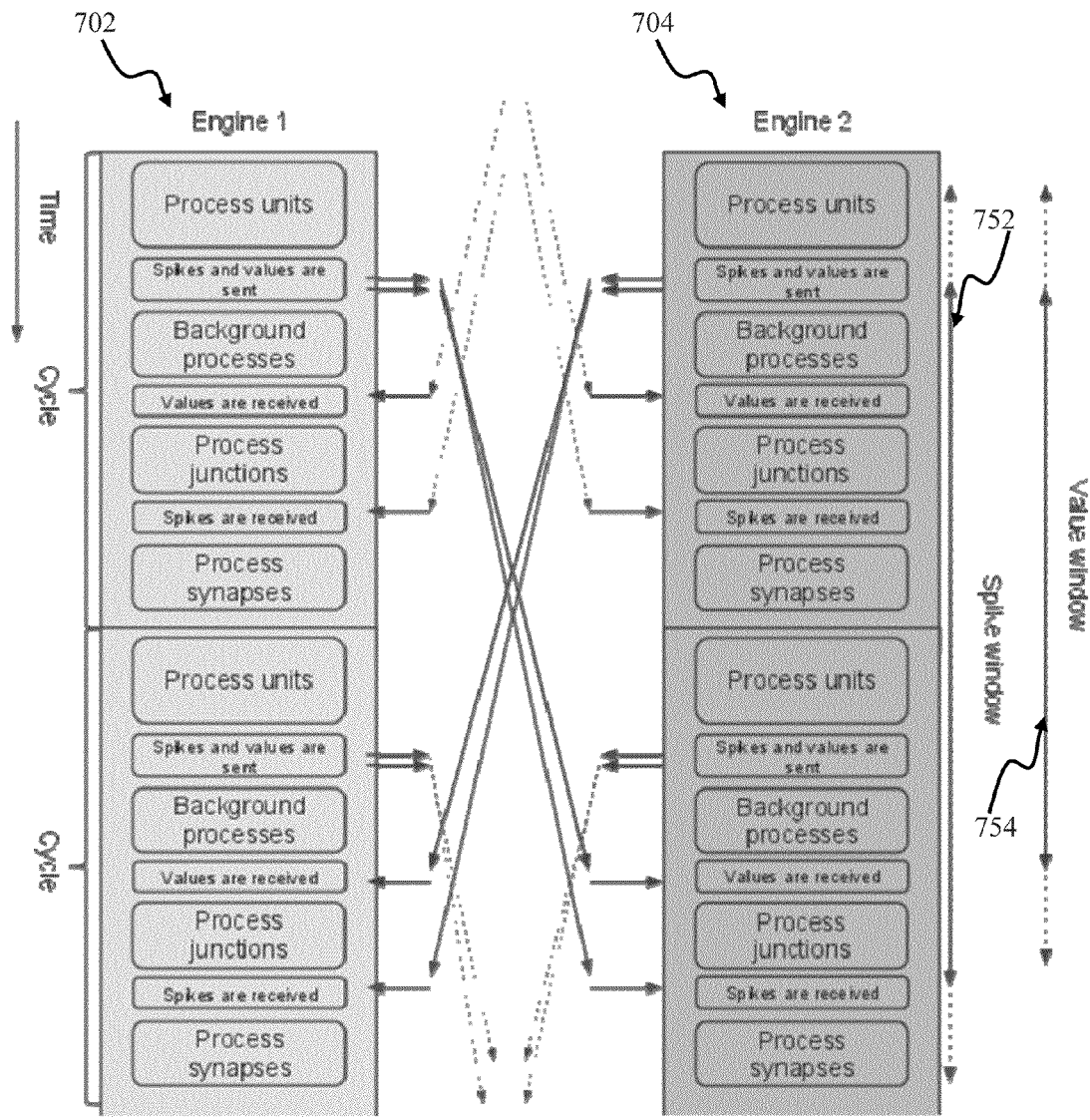
FIG. 7B a block diagram illustrating one embodiment of the synchronous communication of the embodiment of FIG. 7A with a shift (S=1 in both directions), according to one embodiment of the invention.

FIG. 7A illustrates one example of fully synchronous communication between two computation engines 702, 704. The embodiment of FIG. 7 can ensure timely data exchange between the engines 702, 704, and can reduce communications delays, thereby minimizing potential communication channel jamming due to delays that may be associated with heavy and uneven data flows in large, real-time neuronal model simulation runs. In one example, various data transfer optimization are used, which significantly expand the communication bandwidth. In FIG. 7, the event indices and data values are sent through separate ENI channels (denoted by the heavy and thin arrows 706, 708, respectively, in FIG. 7), and have separate receiving points FIG. 7B illustrates one example of synchronous communication with a phase shift of one system clock cycle (simulation step) (S=1 in both directions). The communication channel is used more evenly due to the window overlap (as indicated by the vertical arrows 752, 754 in FIG. 7B, but spikes and values arrive with a delay of 1 ms/step, 4. Sending and Receiving Points The sending point refers to a logical construct of the simulation model which is used to describe the data and events that become available immediately after processing of units during model execution by the computational engine. Similarly, the receiving point is used to describe data staging container used before processing junctions during each simulation cycle. Such an arrangement leaves a short communication window but the following optional optimization may be possible:

The sending driver processes units in a priority order and sends out the data as soon as they become available while other units are still being processed by the engine in parallel.

The receiving driver executes local junctions while still awaiting for the necessary data to arrive.

If the channel sends spike notifications, the computational engine can process synapses from local units before receiving the data on spikes from non-local units.

In such a case the communication window can be significantly expanded (as denoted by dotted arrows in FIG. 7B).

5. An Example of Communications Definitions Using ENI

Listing 7 illustrates one example of an ENI definition file (known to sender/receiver drivers) useful in a network simulation that uses END. It will be appreciated by those skilled in the arts that while the examples below shows the data required to set up a channel, the actual format of that file might change to XML or some other format.

Example 4

Example 4 describes engine simulations where 'Retina' END file sends indices of selected units from class 'RGC' that fired to the engine running 'LGN' END file. Selected elements of class 'exc' are fired. The communication is typically synchronous, synchronization points appear every cycle on both sender and receiver, and the channel has no shift (delay).

Listing 7

```
ENI_ID = 'CommC'
SOURCE_ID = 'Retina'
// id of the source END file (simulation)
TARGET_ID = 'LGN'
// id of the target END file (simulation)
MODE = SYNC
T1=1
// sender sync frequency - when to send data (in simulation cycles)
T2=1
// receiver sync frequency - when to expect data (in simulation cycles )
S=0
// receiver phase shift
FORMAT = INDICES
// Only spiking units will be observed by the channel
SENDER_VALUES = NONE
// only indices will be sent, that is channel will fire target units
RECEIVER_VALUES = NONE
SENDER_CLASS = 'RGC'
RECEIVER_CLASS = 'exc'
NUMBER_OF_UNITS = 500
// How many units will be observed by the channel?
SENDER_UNITS = 84 23 395 39 201 34 ...
RECEIVER_UNITS = 33 45 67 98 18 34 19 ...
```

Example 5

Example 5 illustrates engine simulations where the 'Camera' END will asynchronously send values of 'R, G, B' variables in class Pixel, to variables 'Red,Green,Blue' of class RGC in the Retina END file.

---
Listing 8
---

```
ENI_ID = 'ENI2'
SOURCE_ID = 'Camera'
   // id of the source END file (simulation)
TARGET_ID = 'Retina'
   // id of the target END file (simulation)
MODE = ASYNC
STREAM = NO
   // the receiver will not accumulate data (only the latest data
will be delivered to the engine)
T1=1
   // sender sync frequency - when to send data (in simulation
cycles)
T2=2
   // receiver sync frequency - when to expect data (in simulation
cycles)
FORMAT = NOINDICES
   // All values will be sent every time
SENDER_VALUES = 'R,G,B'
   // values of those variables will be sent
RECEIVER_VALUES = 'Red,Green,Blue'
   // Values of those variables will be updated
SENDER_CLASS = 'Pixel'
RECEIVER_CLASS = 'RGC'
NUMBER_OF_UNITS = 1024
   // How many units will be observed by the channel?
SENDER_UNITS = 1 2 3 4 5 6 7 8 9 10 11 ...
RECEIVER_UNITS = 33 45 67 98 18 34 19 ...
```
---

Figure 13:
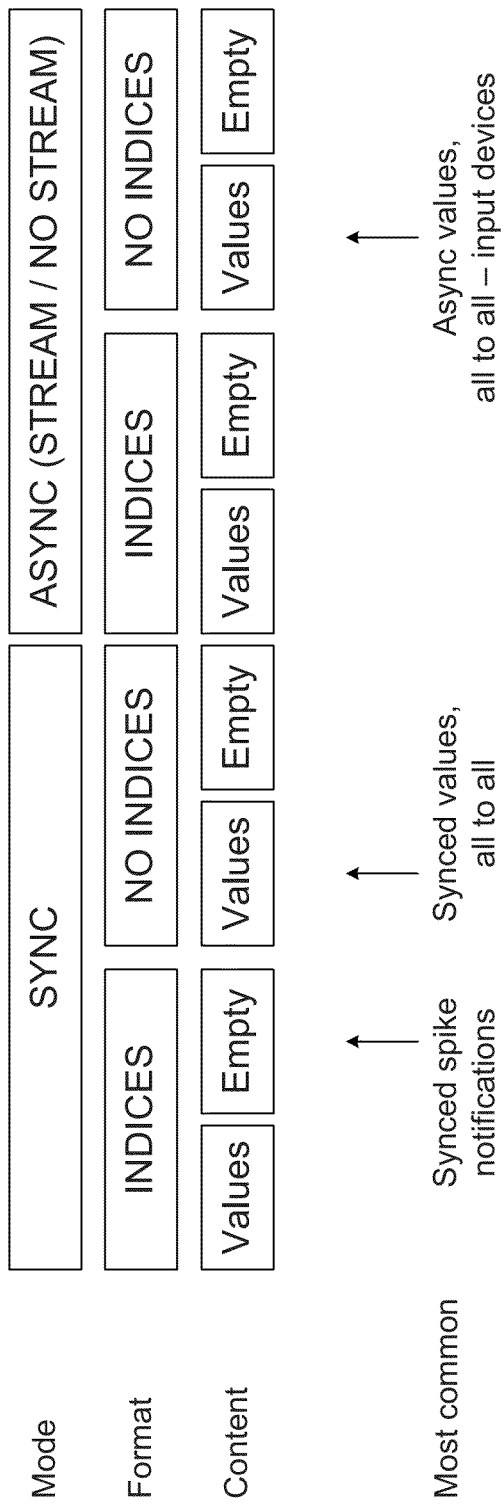
FIG. 13 comprises a table listing possible values of communications parameters.

The table shown in FIG. 13 lists possible values of communications parameters used in Listing 8:

Large Model Partitioning Using ENI

In certain embodiment, many ways exist to handle a large neuro-simulation model (defined, for example, using a high level description format). In one approach, the processing is performed by a single processing computational engine. In another approach, the processing is distributed within a set of several computational engines (computing nodes). In order to achieve efficient workload distribution the model needs to be partitioned. In one example, one large low-level description (END file) of the model is generated and the partitioning is performed by the distributed computational engine. This example offers benefits of real time load adjustment and rebalancing, but is technically more complex and requires an advanced distributed load controller. In another example, the model is partitioned into a set of END files and ENI communication channels, which are executed separately from one another. There is always a way to split a neuro-simulation into parts using ENI, possibly by introducing additional "fake" units.

Figure 8:
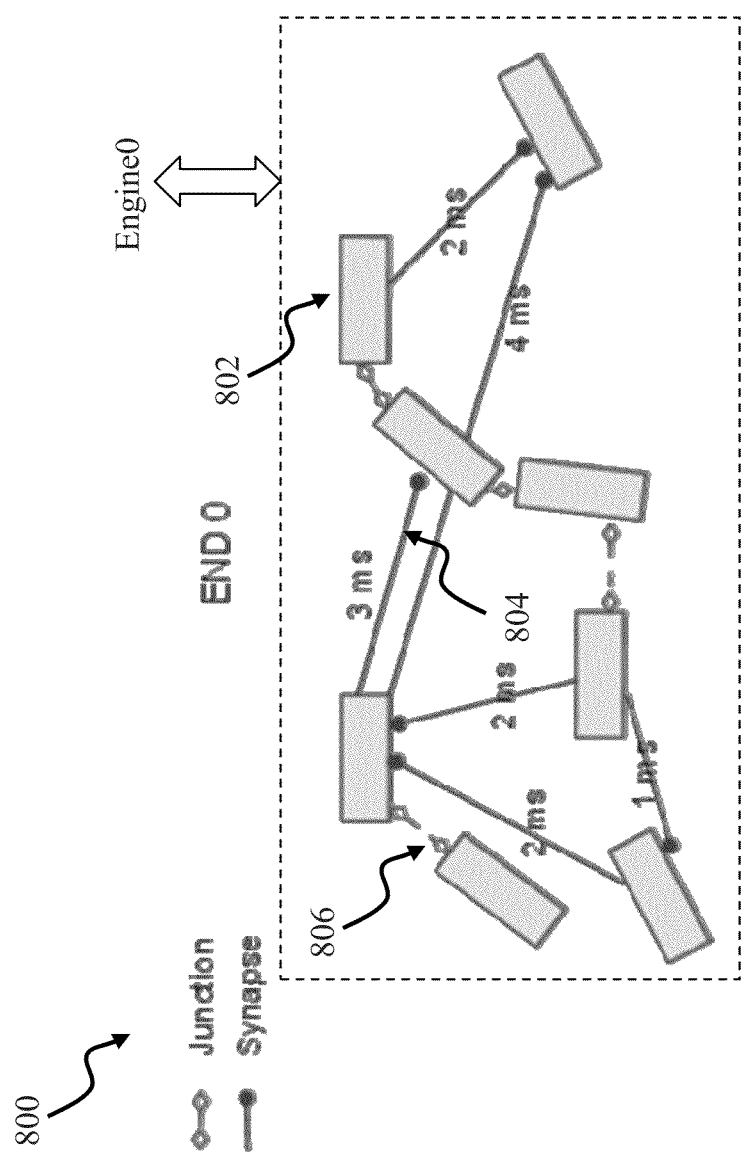
FIG. 8 is a block diagram illustrating a sample communication model with junctions and synapses with delays, according to one embodiment of the invention.
Figure 9:
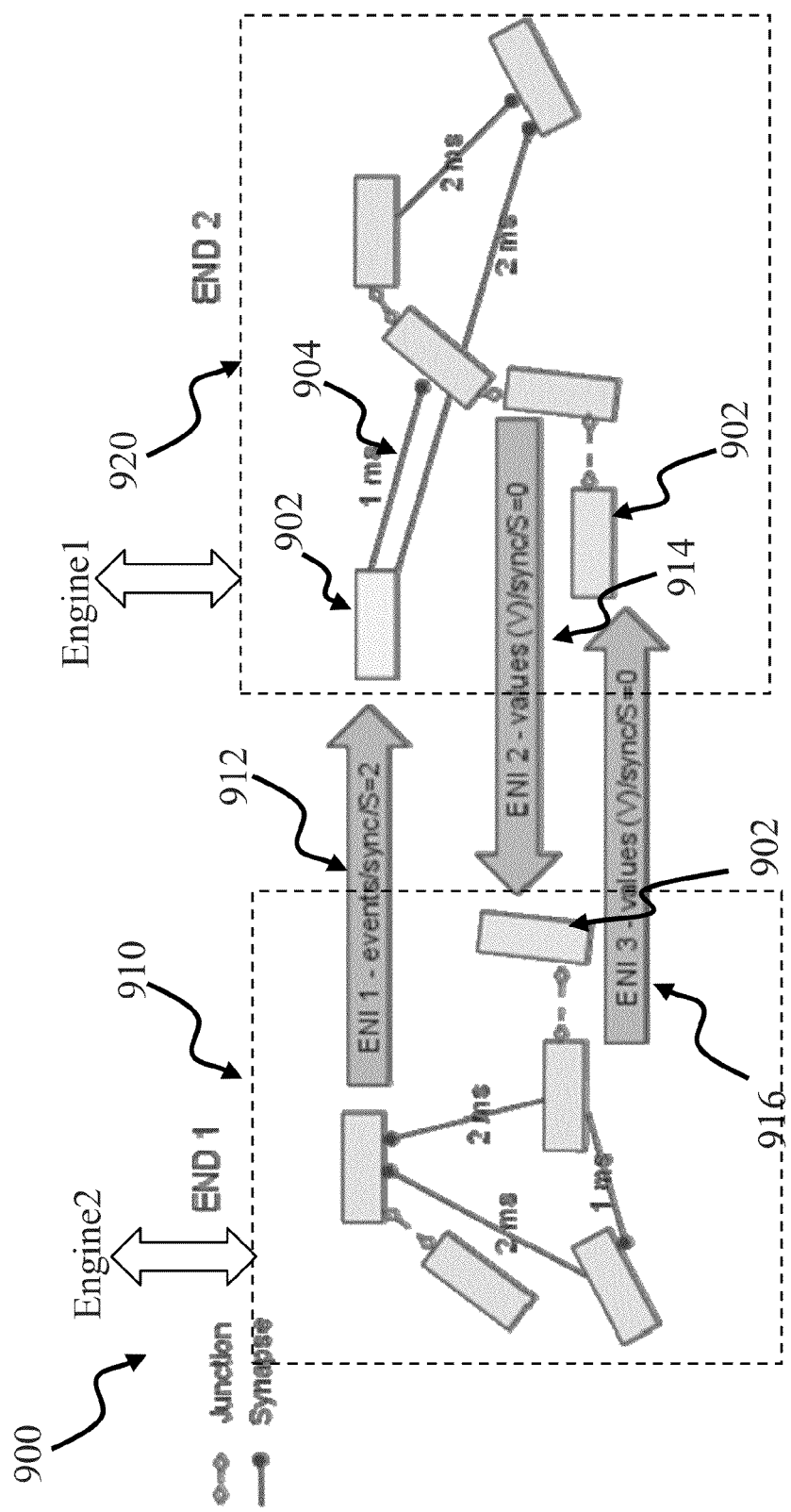
FIG. 9 is a block diagram illustrating one embodiment of communications model comprising ENI channels, according to one embodiment of the invention.

FIGS. 8 and 9 illustrate one example of model partitioning according to certain aspects of the present invention. FIG. 8 shows the END model 800 comprising of several units 802, synapses 804 and junctions 806 and described using the END file END0. The numerals along the synapses 804 denote synaptic delays. The model 800 simulation is executed using a single computational Engine0.

FIG. 9 illustrates partitioning of the model 800 into two partitions 910 and 920, described using the END files END1, END2, respectively. The partitions 910, are interconnected using three ENI interfaces: ENI1, ENI2, END, denoted as 912, 914, 916, respectively in FIG. 9. Some additional 'fake' units have been introduced (rectangles marked as 902). Because the ENI 1 channel has a phase shift S=2, the channel communication delay is compensated by using smaller delays of the target synapses, as illustrated by a comparison of the synapses 804 and 904 in FIGS. 8 and 9, respectively. Note, that such implementation is possible when there are no synapses of minimal delay (e.g., 0) in the original model (the model 800) along the partition line that are replaced by an ENI channel. The compiler from a high-level definition language can take into account the delays while splitting the simulation to optimize communication (e.g. enlarge the communication window, balance the amount of data sent etc.). Simulation of the model 900 is executed using two computational engines: Engine 1 and Engine 2, as illustrated in FIG. 9. The multi-partition simulation 900 is capable of producing the same simulation results, compared to the single partition simulation implementation 800, providing the distributed computational Engine1/Engine2 has sufficient numerical precision to avoid rounding errors.

In other embodiments of partitioned model (not shown), the following features may be implemented:
On the fly ENI channel setup and link negotiation (for dynamic debugging and monitoring);
Support for additional data formats, e.g., analog.
Support for dedicated hardware infrastructure to run ENI;
A convenient and intuitive way to specify ENI format
Parallelization Via Splitting END As described above with respect to the distributed model simulation (such as the partitioned mode 900 of FIG. 9), the model can be split into several partitions (e.g., the partitions 910, 920). Each partition is executed on a single computational engine (engine1, Engine 2 of FIG. 9. In one example, the computational engine comprises a single processing unit (CPU) implementation. In another example, each computational engine comprises multiple processing units (PU), such as, for example, CPU, FPGA, MCU, all running in parallel. Such parallelization enables a substantial increase in the model simulation throughput (that typically scales with the number of parallel PUs). To enable parallel model execution, the simulation domain is divided into several processing blocks (processing domains), each block being assigned to one PU. Each processing block is configured to (i) keep track of local compartments, local spike queues etc.; (ii) store list (table) of incoming "synapses" (not applicable for END 3.0); and store s list of local junctions which can be processed without locking. Compartments are tagged with domain id-s, which must be informed whenever they spike. When such an externally visible compartment spikes, the appropriate information is sent to neighboring domain, which does the rest of processing (synaptic queues etc).

For each step, the voltages of compartments connected via external (remote) junctions are sent to their target domains. Respectively, received voltages are used to compute junction currents.

The only data that the processing domains are exchanging are: (i) the spikes; and (ii) junction voltages (or some other variables that are transmitted across junctions). Since most junctions will be of dendritic type (local), the amount of data in each exchange is typically not large (if the domain division takes dendritic junctions into account).

In another embodiment, a heterogeneous parallelized computational engine is implemented using multi-core symmetric multiprocessors (SMP) hardware. In one example, the SMP implementation also contains a graphical processing unit to implement.

END Engine Embodiments

Figure 10:
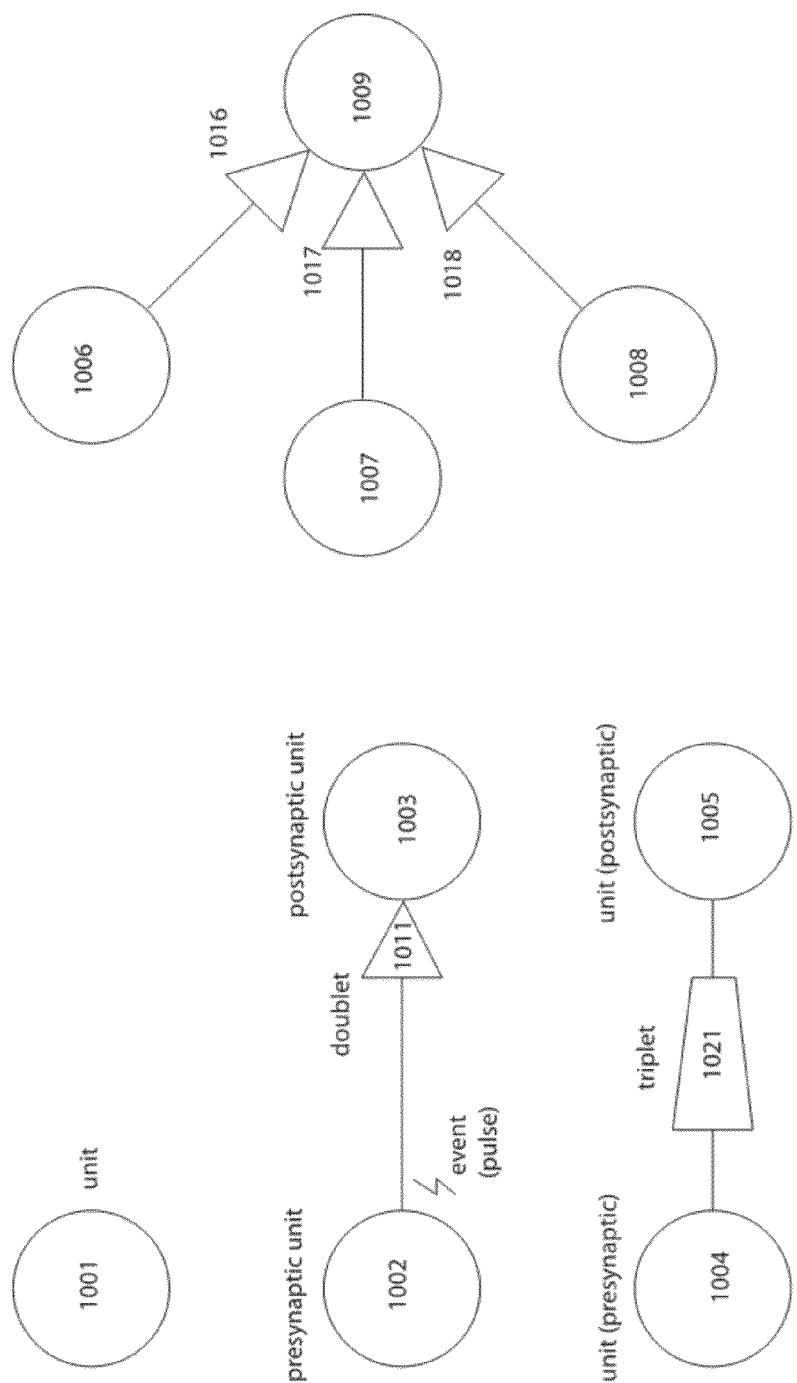
FIG. 10 is a block diagram illustrating various exemplary of the END engine, according to one embodiment of the invention.
Figure 11:
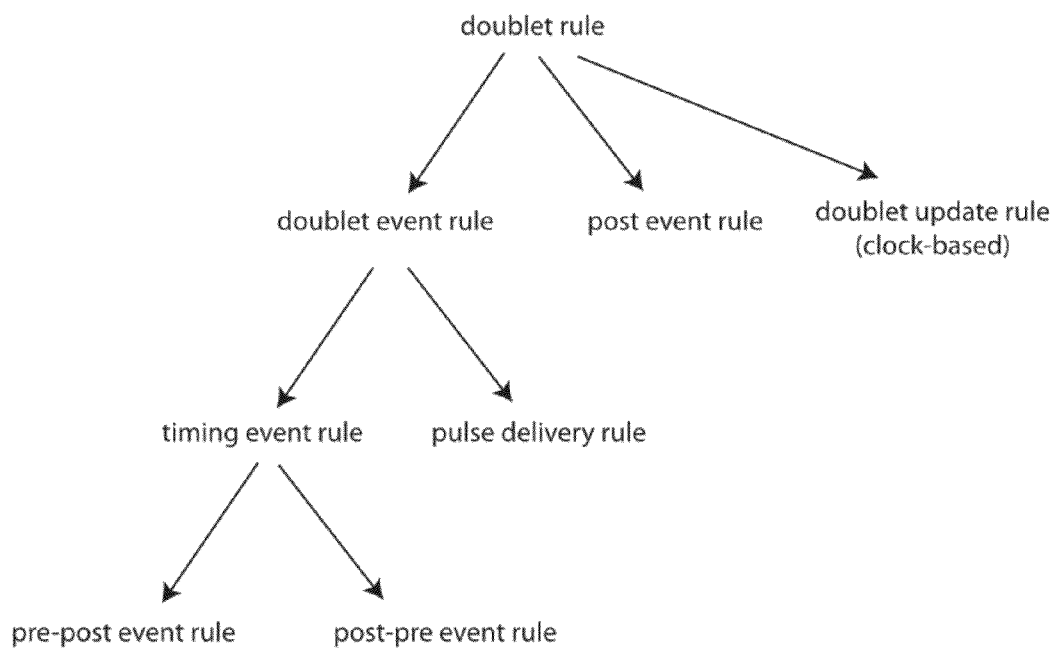
FIG. 11 is a block diagram illustrating logical flow of the doublet event rule according to one embodiment of the invention.
Figure 12:
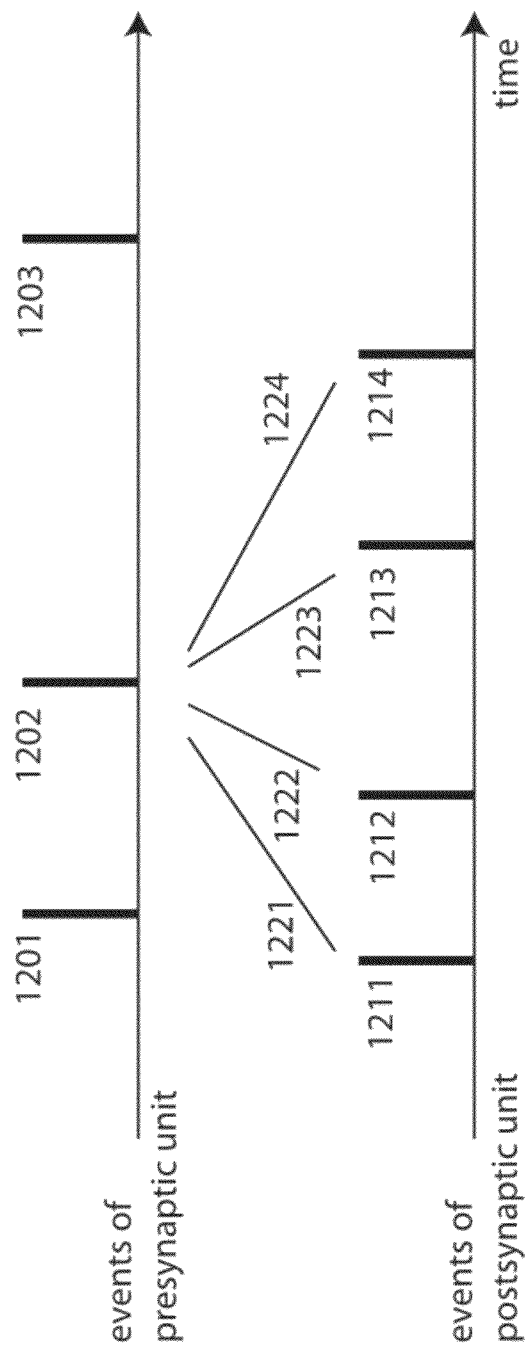
FIG. 12 is a block diagram illustrating a doublet-event rule implementing Spike-Timing Dependent Plasticity (STDP), according to certain aspects of the invention.

FIGS. 10 through 12 describe different exemplary embodiments of the invention that do not depend on the syntax of the END language. FIG. 10 illustrates the three basic structures of the END engine, which can be implemented on a standard CPU, GPU, or in an integrated circuit (e.g., an ASIC). These are the "unit" 1001, the "doublet" 1011, and the "triplet" 1021. The END engine handles the execution of the unit, doublet, and triplet rules and the access to the memories of these elements. The END formats above can be treated as the hardware specification language that would configure a semiconductor circuit having such units, doublets, and triplets that executes a specified neuronal network.

In one example, each basic structure (unit, doublet, and triplet) is implemented as a single thread on a multi-thread processor. In another example, each structure is implemented as a super-unit, super-doublet, and super-triplet that comprises dedicated circuits configured to processes units, doublets, and triplets respectively using time multiplexing (possibly, three different circuits for units, doublets, and triplets).

In one example, the unit 1001 represents a neuron or a part of a neuron, e.g., a dendritic compartment. In another example, the unit 1001 represents a population of neurons, with the activity of the neuron representing a "mean-firing rate" activity of the population or some other mean-field approximation of the activity of the population. Each unit may have its own memory variables and an update rule that describes what operations must be performed on its memory. The operations can be clock-based, i.e., executed every time step of the simulation, or they can be event-based, i.e., executed when certain events are triggered. The unit update rules typically do not involve variables that belong to other units. Hence the execution of the unit update rule is independent on the order of execution of unit update rules of other units, thereby enabling parallel execution of the unit update rules.

Depending on the values of the unit variables, the units may generate events—pulses or spikes—that trigger synaptic events in other units via doublets. For example, a unit 1002 in FIG. 10 can influence unit 1003 via the doublet 1011, which represents a synapse from pre-synaptic neuron (pre-synaptic unit 1002) to post-synaptic neuron (post-synaptic unit 1003).

Units can also have after event update rules that are triggered after the event is triggered. These rules are responsible for modification of unit variables that are due to the events, e.g., the after-spike resetting of voltage variables.

Each doublet, typically has its own memory variables, and it can access variables of the post-synaptic unit. The access includes read and write. Each doublet, has a doublet event rule that makes a change to the doublet memory, to implement synaptic plasticity, and the post-synaptic unit memory, to implement delivery of pulses. The doublet event rule encompasses all the synaptic rules described in the END formats above.

Since multiple doublets (e.g., 1016-1018 in FIG. 10) can connect corresponding multiple pre-synaptic units 1006-1008 to a single post-synaptic unit 1009, it is desirable that the doublets modify the post-synaptic unit memory in parallel or in arbitrary order and the result be order-independent. This is easy to achieve if the operation on the post-synaptic unit memory is atomic addition (as in GPUs), atomic multiplication (which is equivalent to addition via logarithmic transformation), or resetting to a value (with all the doublets trying to reset to the same value). It is also desirable that the post-synaptic unit variable that is being modified by the doublet event rule is not used in the rule. Otherwise, the result may depend on the order of execution of doublet event rules.

In the context of neural computations, it is often desirable to have an axonal conduction delay, so that there is a time-delay between an event generated by a pre-synaptic unit and the execution of the doublet event rule triggered by the unit. The delay can be implemented as a buffer, so that each doublet receives the event with some delay. That is, the END engine registers an event generated by a pre-synaptic unit and puts a special marker into a delay-line queue depending on the magnitude of the delay. The delay is counted down and then the event, transmitted to the doublet for the execution of the doublet event rule.

In certain embodiments, the doublets do not have access to pre-synaptic unit variables. However, in some embodiments, doublets may have access to some pre-synaptic unit variables. In one example, pre-synaptic unit may have variables that are modified only during events triggered by the unit (i.e., event-based memory), and the modification does not depend on the values of the other pre-synaptic unit variables. In such an example, such event-based memory may reside in the pre-synaptic unit memory, or equivalently, it may be treated as if a copy of the event-triggered variables resided at each doublet or shared among doublets The doublet event rule is part of a class of doublet rules, which in some embodiments may also include post event rules and doublet update rules, as illustrated in FIG. 11. The post event rule is a rule that is triggered by a post-synaptic unit and executed for all doublets connecting to the post-synaptic unit. In certain embodiments, the post event rule of a doublet typically depends on the timing of the immediately preceding pre-synaptic event. The doublet update rule is a clock-based rule that is executed for each doublet every time step, i.e., every system clock cycle.

In the embodiment illustrated in FIG. 12, the doublet event rule further comprises a timing event rule that (i) is configured based on the timing of events of the pre-synaptic and post-synaptic units; and (ii) controls the modification of doublet memory variables. The update rule, illustrated in FIG. 12, is at implementing Spike-Timing Dependent Plasticity (STDP)—standard form of plasticity in spiking networks.

The timing event rule can further comprise a pre-post event rule that implements the part of the STDP that corresponds to pre-synaptic neuron firing first (or the spike arriving from the pre-synaptic neuron first) and then the post-synaptic neuron firing thereafter, e.g., the pulses 1202 generated before the pulses 1213, 1214. In the classical STDP this would correspond to the long-term potentiation (LTP) part of the STDP curve. This rule modifies the memory of the doublet based on the timings of the pre-synaptic and at least one subsequent post-synaptic firing, e.g., the pair 1202, 1213 (denoted by the line 1223); it typically depends only on the time difference.

The timing event rule can further comprise a post-pre event rule that implements the long-term depression part of the classical STDP which occurs when the post-synaptic unit fires first and then the pre-synaptic unit fires after that, e.g., like the pulses 1211, 1212 generated before the pulse 1202. This rule modifies the doublet memory based on the relative timing of the pre-synaptic and post-synaptic firing; it typically depends only on the time difference, i.e., on the difference between the timing of the pulses 1212, 1202.

Both, pre-post and post-pre event rules may depend on the values of variables in the post-synaptic unit memory.

In certain embodiments, it may be desirable to allocate memory of doublets according to their pre-synaptic units, so that all doublets having a common pre-synaptic unit are grouped together and allocated consequently in the system memory. This approach can minimize the random access to system memory.

The doublet event rule can also comprise a pulse delivery rule that modifies the values of variables of the post-synaptic unit based on the values of doublet memory and the post-synaptic unit memory.

The description of doublets can be provided by the description of synaptic variables and rules in the END format.

As depicted in FIG. 10, supra, the triplet 1021 connects two units 1004 and 1005. Such a triplet represents a junction in the END format. In one example, the triplet 1021 comprises a gap-junction connection between two neurons. In another example, the triplet 1021 corresponds to a resistance connection that connect two adjacent dendritic compartments of a neuron. In another example, the triplet 1021 is a combination of both junction types. The triplet comprises its own memory and it has access to memories of both units. The triplet further comprises a triplet update rule that is executed every simulation time step. The triplet update rule may update the memory of each triplet and the memory of at least one unit. In certain embodiments, the triplet update rule can update memory of both units. Since it is desirable for such an update to be order-independent, the memory update of the at least one unit is typically performed via atomic addition to a unit variable that does not participate in the triplet update rule.

The description of the triplets can be provided by the description of junctions in the END format.

Certain embodiments can implement purely mean-firing rate models where there are no events, but where each unit transmits a signal to other units via triplet update rule.

Triplets can be allocated in the system memory according to the pre-synaptic unit so that all triplets originating from a common pre-synaptic unit are grouped together. Triplets can also be allocated according to the post-synaptic unit. In certain embodiments, triplets can be allocated in the system memory according to the structure of the neural network. For example, if the neural network has multi-compartmental dendrites, then all triplets responsible for connecting the dendritic compartments, can be allocated optimally as to immunize memory access when the dynamical on the dendritic tree is evaluated during the system clock cycle.

Certain embodiments can implement purely event-driven architectures where units trigger events that deliver pulses to post-synaptic units via doublets. Those units that received at least a single pulse during the clock cycle are tested for an event condition, and if it is satisfied, the after-event rule is executed and corresponding doublet event rules are executed, so that pulses are delivered to other units.

Additional Descriptions of Certain Aspects of the Invention

The foregoing descriptions of the invention are intended to be illustrative and not limiting. For example, those skilled in the art will appreciate that the invention can be practiced with various combinations of the functionalities and capabilities described above, and can include fewer or additional components than described above. Certain additional aspects and features of the invention are further set forth below, and can be obtained using the functionalities and components described in more detail above, as will be appreciated by those skilled in the art after being taught by the present disclosure.

Certain embodiments of the invention provide methods for configuring a neuronal network. Certain embodiments comprise parsing a specification of a system exhibiting aspects of a neuronal network that includes a plurality of independently executable threads. Certain embodiments comprise mapping each of the threads onto a neuronal network comprising a plurality of doublets. In certain embodiments, each doublet is connected to a presynaptic unit and a postsynaptic unit. In certain embodiments, each doublet is configured to modify a memory of the postsynaptic unit responsive to events received from the presynaptic unit. Certain embodiments comprise defining operational characteristics of the plurality of doublets and their corresponding presynaptic and postsynaptic units. In certain embodiments, defining the operational characteristics includes configuring a doublet event rule for each doublet that determines how the each doublet updates the memory of the postsynaptic unit, wherein execution of doublet event rules is order-independent. In certain embodiments, defining the operational characteristics includes configuring a unit update rule for each unit that controls the response of the each unit to memory updates initiated by a doublet. In certain embodiments, execution of the unit update rules is order-independent.

In certain embodiments, configuring doublet event rules includes configuring each of the doublet event rules to be executed within a time step during which an event is received. In certain embodiments, the time step has a duration determined by a system clock. In certain embodiments, each presynaptic unit maintains an event condition that controls transmission of events to a connected doublet. In certain embodiments, at least one doublet has a doublet memory. In certain embodiments, configuring the rules includes configuring the doublet event rule for the at least one doublet that determines how the at least one doublet updates its doublet memory. In certain embodiments, the doublet event rule for each doublet includes a timing event rule that controls modification of a memory of the each doublet based on timing of pulses associated with one or more of the plurality of units. In certain embodiments, execution of the doublet event rule for each doublet is triggered by an event received from a presynaptic unit.

In certain embodiments, the neuronal network further comprises a plurality of triplets, each triplet adapted to access memory of a pair of units. In certain embodiments, each triplet has a memory and is configured to modify its own memory and the memory of at least one of the pair of units. In certain embodiments, mapping each of the threads onto a neuronal network further comprises configuring triplet update rules that control updates to memories of triplets and their corresponding pairs of triplet-connected units, wherein execution of triplet update rules is order-independent. In certain embodiments, each step of interconnecting pluralities of units. In certain embodiments, each step of configuring rules are performed in accordance with a directed graph representative of the neuronal network. In certain embodiments, the step of mapping includes producing an abstracted hardware mapping representing the neuronal network. In certain embodiments, the hardware mapping is described in a hardware description language.

Certain embodiments comprise configuring a semiconductor integrated circuit to implement the neuronal network. In certain embodiments, mapping each of the threads onto a neuronal network comprises providing one or more target libraries that describe units and doublets as constructs in an abstracted description language that is independent of target characteristics. In certain embodiments, mapping each of the threads onto a neuronal network comprises mapping each thread onto abstracted units and doublets to obtain an abstracted description of the neuronal network. Certain embodiments comprise generating a definition of a physical implementation of the neuronal network using a synthesis tool from the abstracted description of the neuronal network. In certain embodiments, configuring the rules comprises providing one or more rule libraries that describe the rules in an abstracted programming language. In certain embodiments, configuring the rules comprises generating abstracted rules using the one or more rule libraries and coded in the abstracted programming language. Certain embodiments comprise configuring the physical implementation of the neuronal network by compiling the abstracted rules into object code consistent with the physical implementation of the neuronal network.

Certain embodiments of the invention provide a configured neuronal network, comprising a system clock defining a sequence of time intervals. Certain embodiments comprise a plurality of elements consisting of units, doublets and triplets. In certain embodiments, each of the units has a memory updated according to a unit update rule of the unit. In certain embodiments, a doublet event rule configured for each doublet causes the memory of a postsynaptic unit to be updated in response to an event received from a presynaptic unit. In certain embodiments, each triplet is configured to access the memory of two units and to update the memory of at least one of the two units in accordance with a corresponding triplet update rule. Certain embodiments comprise a mapper that parses a specification of a neuronal network, and maps each of a plurality of independently executable threads of the neuronal network onto the units, doublets and triplets.

In certain embodiments, the mapper configures the unit update rules, the doublet event rules and the triplet update rules. In certain embodiments, the execution of unit update rules is order-independent and at least partially executed once in every time interval. In certain embodiments, for those doublets that respond to an event during a particular time interval, execution of the doublet event rules corresponding to those doublets is order independent. In certain embodiments, execution of triplet update rules is order-independent and at least partially executed once in every time interval. In certain embodiments, updates to the memory of the units are made by atomic addition. In certain embodiments, for the each doublet, the execution of the corresponding doublet event rule is triggered in response to a change in the memory of the presynaptic unit. In certain embodiments, for at least one doublet, there is a delay between occurrence of changes in the memory of its corresponding presynaptic unit and updates to the memory of its corresponding postsynaptic unit. In certain embodiments, at least one doublet has a memory that is updated in response to events received from its corresponding presynaptic unit. In certain embodiments, the memory of the postsynaptic unit corresponding to the each doublet is updated based on the content of the memory of the each doublet.

In certain embodiments, the doublet event rule for each doublet includes a timing event rule that controls modification of the memory of the each doublet. In certain embodiments, the specification comprises a directed graph.

While certain aspects of the invention are described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of configuring a neuronal network, the method comprising:
    parsing a specification of a system exhibiting aspects of a neuronal network that includes a plurality of independently executable threads;
    mapping individual ones of the plurality of independently executable threads onto a neuronal network comprising a plurality of doublets, individual doublet being connected to a presynaptic unit and a postsynaptic unit, wherein a given doublet is configured to modify a memory of the postsynaptic unit responsive to events received from the presynaptic unit; and
    defining operational characteristics of the plurality of doublets and their corresponding presynaptic and postsynaptic units, wherein:
    defining the operational characteristics includes:
        for the given doublet configuring a doublet event rule that determines how the given doublet is configured to update the memory of the postsynaptic unit, wherein execution of doublet event rules is order-independent; and
        for a given unit configuring a unit update rule that controls the response of the given unit to memory updates initiated by a doublet, wherein execution of the unit update rules is order-independent; and
    wherein a given presynaptic unit is configured to maintain an event condition that controls transmission of events to a respective connected doublet.

2. The method of claim 1, wherein the doublet event is configured to be executed within a time step during which an event is received, the time step having a duration determined by a system clock.

3. The method of claim 1, wherein at least one doublet has a doublet memory and configuring the rules includes configuring the doublet event rule for the at least one doublet that determines how the at least one doublet updates its doublet memory.

4. The method of claim 1, wherein the doublet event rule for a given doublet includes a timing event rule that controls modification of a memory of the given doublet based on timing of pulses associated with one or more of the plurality of units.

5. The method of claim 4, wherein execution of the doublet event rule for the given doublet is triggered by an event received from a presynaptic unit.

6. The method of claim 5, wherein for at least one doublet, there is a delay between occurrence of changes in the memory of its corresponding presynaptic unit and updates to the memory of its corresponding postsynaptic unit.

7. The method of claim 1, wherein the neuronal network further comprises a plurality of triplets, individual triplets adapted to access memory of a pair of units, wherein individual triplet comprises a memory and is configured to modify its own memory and the memory of at least one of the pair of units, and wherein mapping individual threads onto a neuronal network further comprises configuring triplet update rules that control updates to memories of triplets and their corresponding pairs of triplet-connected units, wherein execution of triplet update rules is order-independent.

8. The method of claim 7, wherein interconnection of individual ones of the plurality of units, and configuring individual ones of the rules is performed in accordance with a directed graph representative of the neuronal network.

9. The method of claim 8, wherein the step of mapping includes producing an abstracted hardware mapping representing the neuronal network.

10. The method of claim 8, wherein the hardware mapping is described in a hardware description language.

11. The method of claim 1, further comprising configuring a semiconductor integrated circuit to implement the neuronal network.

12. A method of configuring a neuronal network, the method comprising:
parsing a specification of a system exhibiting aspects of a neuronal network that includes a plurality of independently executable threads;
mapping individual ones of the plurality of independently executable threads onto a neuronal network comprising a plurality of doublets, a given doublet being connected to a presynaptic unit and a postsynaptic unit, wherein the given doublet is configured to modify a memory of the postsynaptic unit responsive to events received from the presynaptic unit; and
defining operational characteristics of the plurality of doublets and their corresponding presynaptic and postsynaptic units, wherein
defining the operational characteristics includes:
for the given doublet configuring a doublet event rule that determines how the given doublet is configured to update the memory of the postsynaptic unit, wherein execution of doublet event rules is order-independent; and
for a given unit configuring a unit update rule that controls the response of the given unit to memory updates initiated by a doublet, wherein execution of the unit update rules is order-independent; and
wherein mapping individual ones of the plurality of independently executable threads onto a neuronal network comprises:
providing one or more target libraries that describe units and doublets as constructs in an abstracted description language that is independent of target characteristics; and
mapping individual ones of the plurality of independently executable threads onto the abstracted units and doublets to obtain an abstracted description of the neuronal network.

13. The method of claim 12, further comprising generating a definition of a physical implementation of the neuronal network using a synthesis tool from the abstracted description of the neuronal network.

14. The method of claim 12, wherein configuring the rules comprises:
providing one or more rule libraries that describe the rules in an abstracted programming language; and
generating abstracted rules using the one or more rule libraries and coded in the abstracted programming language.

15. The method of claim 12, further comprising configuring the physical implementation of the neuronal network by compiling the abstracted rules into object code consistent with the physical implementation of the neuronal network.

16. A system for configuring a neuronal network, the system comprising:
one or more processors configured to execute computer program modules, the computer program modules comprising:
a system clock module configured to determine a sequence of time intervals;
an elements module configured to provide a plurality of elements consisting of units, doublets and triplets, individual units having a memory updated according to a unit update rule of the unit, wherein a doublet event rule configured for a given doublet causes the memory of a postsynaptic unit to be updated in response to an event received from a presynaptic unit, and wherein a given triplet is configured to access the memory of two units and to update the memory of at least one of the two units in accordance with a corresponding triplet update rule; and
a mapper module configured to parse a specification of a neuronal network, and maps individual ones of a plurality of independently executable threads of the neuronal network onto the units, doublets and triplets,
wherein:
the mapper module configures the unit update rules, the doublet event rules and the triplet update rules,
the execution of unit update rules is order-independent and at least partially executed once in every time interval,
for those doublets that respond to an event during a particular time interval, execution of the doublet event rules corresponding to those doublets is order independent,
execution of triplet update rules is order-independent and at least partially executed once in every time interval,
updates to the memory of the units are made by atomic addition; and
for the given doublet, the execution of the corresponding doublet event rule is triggered in response to a change in the memory of the presynaptic unit.

17. The neuronal network of claim 16, wherein for at least one doublet, there is a delay between occurrence of changes in the memory of its corresponding presynaptic unit and updates to the memory of its corresponding postsynaptic unit.

18. The neuronal network of claim 16, wherein at least one doublet has a memory that is updated in response to events received from its corresponding presynaptic unit, and wherein the memory of the postsynaptic unit corresponding to the given doublet is updated based on the content of the memory of the given doublet.

19. The neuronal network of claim 18, wherein the doublet event rule for the given doublet includes a timing event rule that controls modification of the memory of the given doublet.

20. The neuronal network of claim 16, wherein the specification comprises a directed graph.

21. The neuronal network of claim 16, wherein configuring the rules comprises:
providing one or more rule libraries that describe the rules in an abstracted programming language; and
generating abstracted rules using the one or more rule libraries and coded in the abstracted programming language.

* * * * *